US007632617B2

(12) United States Patent
Qi et al.

(10) Patent No.: US 7,632,617 B2
(45) Date of Patent: Dec. 15, 2009

(54) SILANE-PHENOL COMPOUND, OVERCOAT FORMULATION, AND ELECTROPHOTOGRAPHIC IMAGING MEMBER

(75) Inventors: Yu Qi, Oakville (CA); Nan-Xing Hu, Oakville (CA); Ah-Mee Hor, Mississauga (CA)

(73) Assignee: Xerox Corporation, Norwalk, CT (US)

( * ) Notice: Subject to any disclaimer, the term of this patent is extended or adjusted under 35 U.S.C. 154(b) by 666 days.

(21) Appl. No.: 11/184,390

(22) Filed: Jul. 19, 2005

(65) Prior Publication Data

US 2007/0020540 A1 Jan. 25, 2007

(51) Int. Cl.
*G03G 5/07* (2006.01)

(52) U.S. Cl. ........................................ 430/66; 430/58.2

(58) Field of Classification Search ................ 430/58.2, 430/66

See application file for complete search history.

(56) References Cited

U.S. PATENT DOCUMENTS 3,121,006 A 2/1964 Middleton et al.
3,590,000 A 6/1971 Palermiti et al.
3,849,182 A 11/1974 Hagenbach
3,900,588 A 8/1975 Fisher
3,931,267 A 1/1976 Brode
4,264,672 A 4/1981 Taylor-Brown et al.
4,265,990 A 5/1981 Stolka et al.
4,298,697 A 11/1981 Baczek et al.
4,338,390 A 7/1982 Lu
4,558,108 A 12/1985 Alexandru et al.
4,560,535 A 12/1985 Bouchée
4,560,635 A 12/1985 Hoffend et al.
4,588,108 A 5/1986 Knez et al.
4,752,549 A * 6/1988 Otsuka et al. .............. 430/59.6
5,368,967 A 11/1994 Schank et al.
5,567,833 A 10/1996 Iwahara et al.
5,681,679 A 10/1997 Schank et al.
5,702,854 A 12/1997 Schank et al.
5,709,974 A 1/1998 Yuh et al.
2004/0062568 A1* 4/2004 Nukada et al. .............. 399/159
2004/0101774 A1 5/2004 Yoshimura et al.
2004/0126715 A1 7/2004 Larson et al.

FOREIGN PATENT DOCUMENTS

JP 2003-186231 * 7/2003

OTHER PUBLICATIONS

English translation of JP 2003-186231 published Jul. 2003.*

* cited by examiner

*Primary Examiner*—Mark F Huff
*Assistant Examiner*—Peter L Vajda
(74) *Attorney, Agent, or Firm*—Fay Sharpe LLP

(57) ABSTRACT

Provided are a silane-phenol compound, a crosslinked siloxane-phenolic protective overcoat layer thereof, and an electrophotographic imaging member such as photoreceptor. The silane-phenol compound comprises (i) a phenol group and (ii) a silane group selected from the group consisting of alkoxysilyl, arylalkoxysilyl, aryloxysilyl, alkylaryloxysilyl, and combination thereof. The silicone overcoat is made from a formulation comprising the silane-phenol compound and a hydroxymethylated hole transport compound. The crosslinked siloxane-phenolic overcoat may be used to manufacture an electrophotographic imaging member such as photoreceptor with improved properties such as abrasive resistance, good image quality and cleanability, etc.

15 Claims, 3 Drawing Sheets

10
18
16
14
12

SILANE-PHENOL COMPOUND, OVERCOAT FORMULATION, AND ELECTROPHOTOGRAPHIC IMAGING MEMBER

CROSS REFERENCE TO RELATED APPLICATIONS

This application also relates to U.S. patent application Ser. No. 11/184,385, filed Jul. 19, 2005, now U.S. Pat. No. 7,470, 493, the disclosure of which is hereby incorporated by reference in its entirety.

BACKGROUND

The present disclosure is generally directed, in various embodiments, to silane-phenol compounds, crosslinked siloxane-phenolic protective overcoat layers comprising the hydralysates and condensates of the silane-phenol compounds and hydroxymethylated hole transport compounds, and electrophotographic imaging members comprising such crosslinked siloxane-phenolic protective overcoat layers.

In the art of xerography, or electrophotographic printing/copying, an electrophotographic imaging member such as photoreceptor is electrostatically charged. For optimal image production, the photoreceptor should be uniformly charged across its entire surface. The photoreceptor is then exposed to a light pattern of an input image to selectively discharge the surface of the photoreceptor in accordance with the image. The resulting pattern of charged and discharged areas on the photoreceptor forms an electrostatic charge pattern (i.e., a latent image) conforming to the input image. The latent image is developed by contacting it with finely divided electrostatically attractable powder called toner. Toner is held on the image areas by electrostatic force. The toner image may then be transferred to a substrate or support member, and the image is then affixed to the substrate or support member by a fusing process to form a permanent image thereon. After transfer, excess toner left on the photoreceptor is cleaned from its surface, and residual charge is erased from the photoreceptor.

Electrophotographic photoreceptors can be provided in a number of forms. For example, the photoreceptors can be a homogeneous layer of a single material, such as vitreous selenium, or it can be a composite layer containing a photoconductive layer and another material. In addition, the photoreceptor can be layered. Current layered photoreceptors generally have at least a flexible substrate support layer and two active layers. These active layers generally include a charge generating layer containing a light absorbing material, and a charge transport layer containing electron donor molecules. These layers can be in any order, and sometimes can be combined in a single or a mixed layer. The flexible substrate support layer can be formed of a conductive material. Alternatively, a conductive layer can be formed on top of a nonconductive flexible substrate support layer.

A photoreceptor can be in a rigid drum configuration or in a flexible belt configuration. The belt can be either seamless or seamed.

Typical photoreceptor drums comprise a charge transport layer and a charge generating layer coated over a rigid conducting substrate support drum. For example, many advanced imaging systems are based on the use of small diameter photoreceptor drums. The use of small diameter drums places a premium on photoreceptor life. A major factor limiting photoreceptor life in copiers and printers is wear. The use of small diameter drum photoreceptors exacerbates the wear problem because, for example, 3 to 10 revolutions are required to image a single letter size page. Multiple revolutions of a small diameter drum photoreceptor to reproduce a single letter size page can require up to 1 million cycles from the photoreceptor drum to obtain 100,000 prints, a desirable goal for commercial systems.

For low volume copiers and printers, bias charging rolls (BCR) are desirable because little or no ozone is produced during image cycling. However, the micro corona generated by the BCR during charging, damages the photoreceptor, resulting in rapid wear of the imaging surface, e.g., the exposed surface of the charge transport layer. For example, wear rates can be as high as about 16 μm per 100,000 imaging cycles. Similar problems are encountered with bias transfer roll (BTR) systems. One approach to achieving longer photoreceptor drum life is to form a protective overcoat on the imaging surface, e.g. the charge transporting layer of a photoreceptor. This overcoat layer must satisfy many requirements, including transporting holes, resisting image deletion, resisting wear, avoidance of perturbation of underlying layers during coating, and etc.

For flexible photoreceptor belts, the charge transport layer and charge generating layer are coated on top of a flexible substrate support layer. To ensure that the photoreceptor belts exhibit sufficient flatness, an anticurl backing layer can be coated onto the back side of the flexible substrate support layer to counteract upward curling and ensure photoreceptor flatness. The flexible photoreceptor belts are repeatedly cycled to achieve high speed imaging. As a result of this repetitive cycling, the outermost layer of the photoreceptor experiences a high degree of frictional contact with other machine subsystem components used to clean and/or prepare the photoreceptor for imaging during each cycle. When repeatedly subjected to cyclic mechanical interactions against the machine subsystem components, photoreceptor belts can experience severe frictional wear at the outermost organic photoreceptor layer surface that can greatly reduce the useful life of the photoreceptor. Ultimately, the resulting wear impairs photoreceptor performance and thus image quality.

In U.S. Pat. No. 5,702,854 to Schank et al. issued Dec. 30, 1998, an electrophotographic imaging member is disclosed including a supporting substrate coated with at least a charge generating layer, a charge transport layer and an overcoating layer. The overcoating layer comprises a dihydroxy arylamine dissolved or molecularly dispersed in a crosslinked polyamide matrix. The overcoating layer is formed by crosslinking a crosslinkable coating composition including a polyamide containing methoxy methyl groups attached to amide nitrogen atoms, a crosslinking catalyst and a dihydroxy amine, and heating the coating to crosslink the polyamide. The electrophotographic imaging member may be imaged in a process involving uniformly charging the imaging member, exposing the imaging member with activating radiation in image configuration to form an electrostatic latent image, developing the latent image with toner particles to form a toner image, and transferring the toner image to a receiving member.

In U.S. Pat. No. 5,681,679 issued to Schank, et al., a flexible electrophotographic imaging member is disclosed including a supporting substrate and a resilient combination of at least one photoconductive layer and an overcoat layer, the at least one photoconductive layer comprising a hole transporting arylamine siloxane polymer and the overcoat comprising a crosslinked polyamide doped with a dihydroxy amine. This imaging member may be utilized in an imaging process including forming an electrostatic latent image on the imaging member, depositing toner particles on the imaging member in conformance with the latent image to form a toner image, and transferring the toner image to a receiving member.

Yuh et al. have disclosed an electrophotographic imaging member in U.S. Pat. No. 5,709,974 issued on Jan. 20, 1998. The electrophotographic imaging member includes a charge generating layer, a charge transport layer and an overcoat layer. The transport layer includes a charge transporting aromatic diamine molecule in a polystyrene matrix and the overcoat layer includes a hole transporting hydroxy arylamine compound having at least two hydroxy functional groups and a polyamide film forming binder capable of forming hydrogen bonds with the hydroxy functional groups of the hydroxy arylamine compound.

In U.S. Pat. No. 5,368,967 issued to Schank et al., an electrophotographic imaging member is disclosed comprising a substrate, a charge generating layer, a charge transport layer, and an overcoat layer comprising a small molecule hole transporting arylamine having at least two hydroxy functional groups, a hydroxy or multihydroxy triphenyl methane and a polyamide film forming binder capable of forming hydrogen bonds with the hydroxy functional groups the hydroxy arylamine and hydroxy or multihydroxy triphenyl methane. This overcoat layer may be fabricated using an alcohol solvent. This electrophotographic imaging member may be utilized in an electrophotographic imaging process. Specific materials including Elvamide polyamide and N,N'-diphenyl-N,N'-bis(3-hydroxyphenyl)-[1,1'-biphenyl]-4,4'-diamine and bis-[2-methyl-4-(N-2-hydroxyethyl-N-ethyl-aminophenyl)]-phenylmethane are disclosed in this patent.

Crosslinked siloxane overcoat layers have demonstrated good potentials for extrinsic life extension of, for example, organic photoreceptors. Owing to its crosslinked siloxane structure, the overcoat layer offers excellent abrasive, scratching and marring resistance. However, several shortcomings are also associated with crosslinked siloxane-containing overcoat layers. In particular, in electrophotographic photoreceptors in which the overcoat layer is the crosslinked siloxane material, image deletion occurs when the environmental contaminants around the charging device in the xerographic engine interact with the overcoat. Furthermore, another shortcoming associated with the siloxane-containing overcoat layers is the high torque required to rotate the coated photoreceptor against a cleaning blade. In addition, because the crosslinked siloxane overcoat layers are typically prepared by sol-gel processes, shrinkage of the applied layer occurs, which strains the resulting materials. Although attempts have been made to solve these problems by modifying various component materials, such modifications typically present trade-offs in terms of improving one property while deteriorating another property. The main causes are believed to be poor micromechanical properties and sensitive to corona effluence.

As such, new protective overcoat designs are needed to manufacture an electrophotographic imaging member such as photoreceptor with improved properties such as image deletion resistance, cleanability, low friction, among others.

BRIEF DESCRIPTION

In one exemplary embodiment, a silane-phenol compound is disclosed, which comprises (i) a phenol group and (ii) a silane group selected from the group consisting of alkoxysilyl, arylalkoxysilyl, aryloxysilyl, alkylaryloxysilyl, and combination thereof.

In another exemplary embodiment, a crosslinked siloxane-phenolic protective overcoat layer for electrophotographic imaging member is provided; the overcoat layer comprises the hydrolysates and condensates of a hydroxymethylated hole transport compound and a silane-phenol compound comprising (i) a phenol group and (ii) a silane group selected from the group consisting of alkoxysilyl, arylalkoxysilyl, aryloxysilyl, alkylaryloxysilyl, and combinations thereof.

In still another exemplary embodiment, an electrophotographic imaging member such as photoreceptor is provided; the electrophotographic imaging member comprises a substrate, a charge generating layer, a charge transport layer, and a crosslinked siloxane-phenolic protective overcoat layer comprising the product of hydrolysis and condensation of a hydroxymethylated hole transport compound and a silane-phenol compound comprising (i) a phenol group and (ii) a silane group selected from the group consisting of alkoxysilyl, arylalkoxysilyl, aryloxysilyl, alkylaryloxysilyl, and combination thereof.

These and other non-limiting embodiments will be more particularly described with regard to the drawings and detailed description set forth below.

BRIEF DESCRIPTION OF THE DRAWINGS

The following is a brief description of the drawings which is presented for the purposes of illustrating the disclosure set forth herein and not for the purposes of limiting the same.

DETAILED DESCRIPTION

Figure 1:
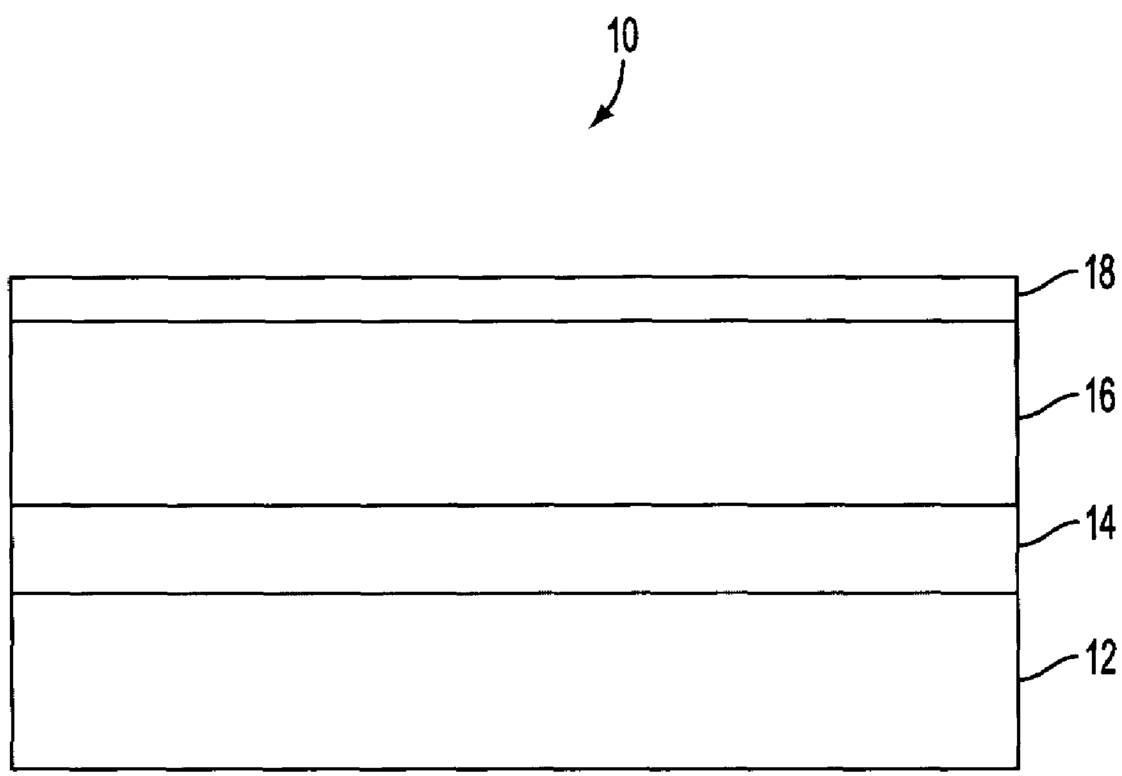
FIG. 1 is a schematic cross-sectional view of a photoconductive imaging member in accordance with the present invention.
Figure 2:
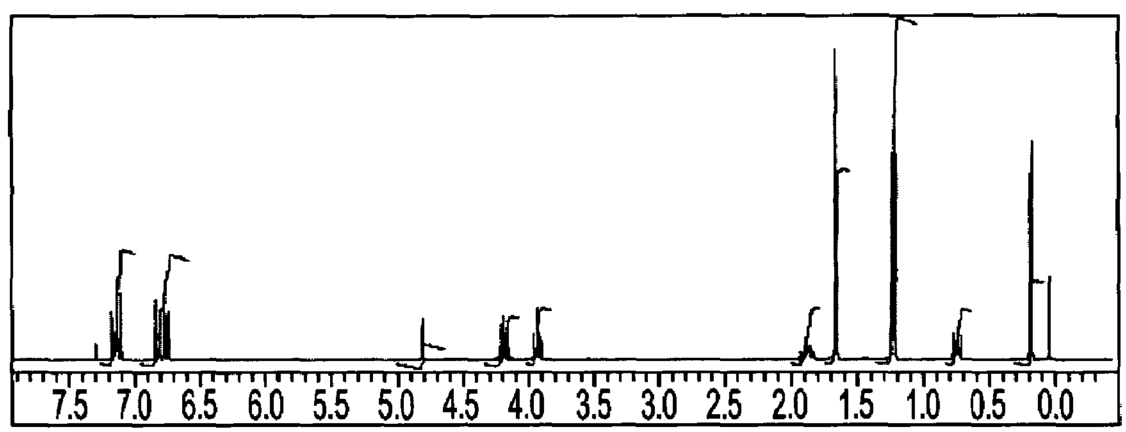
FIG. 2 shows the $^{1}$H NMR spectrum of an exemplary silane-phenol compound in an embodiment of the present disclosure.
Figure 3:
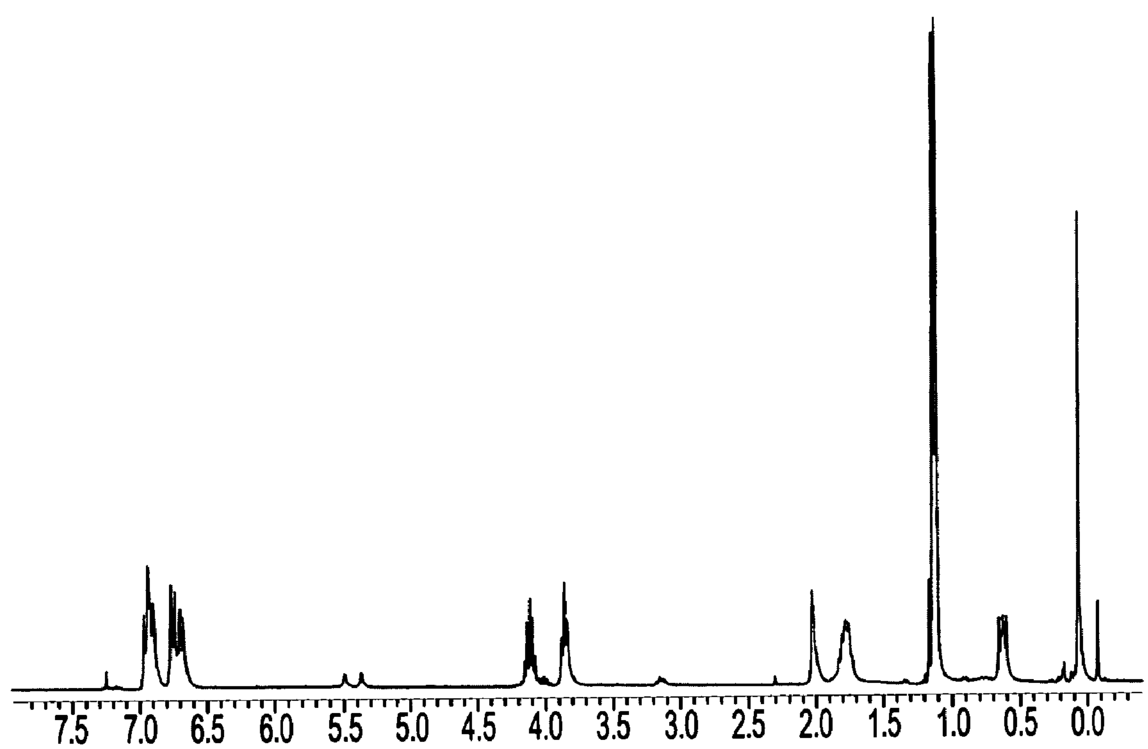
FIG. 3 shows the $^{1}$H NMR spectrum of another exemplary silane-phenol compound in an embodiment of the present disclosure.

The present disclosure relates to a photoconductive imaging member comprising a substrate, a charge generation layer, a charge transport layer, and an overcoating layer disposed over the charge transport layer. The overcoating layer, or overcoat, is formed from crosslinking of the hydrolysates and condensates of a silane-phenol compound and a hydroxymethylated hole transport compound. The present disclosure also relates to a process for forming the photoconductive imaging member and the overcoating layer.

Also included within the scope of the present disclosure are methods of imaging and printing with the photoresponsive devices illustrated herein. These methods generally involve the formation of an electrostatic latent image on the imaging member, followed by developing the image with a toner composition comprised, for example, of thermoplastic resin, colorant, such as pigment, charge additive, and surface additives, reference U.S. Pat. Nos. 4,560,635; 4,298,697; and, 4,338,390, the disclosures of which are totally incorporated herein by reference, subsequently transferring the image to a suitable substrate, and permanently affixing the image thereto.

A more complete understanding of the processes and apparatuses disclosed herein can be obtained by reference to the accompanying drawings. These figures are merely schematic representations based on convenience and the ease of demonstrating the present development, and are, therefore, not intended to indicate relative size and dimensions of the imaging members or components thereof.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to component of like function.

With reference to FIG. 1, a photoconductive imaging member in accordance with the present disclosure is shown. Photoconductive imaging member 10 comprises a substrate 12, a charge generating or photogenerating layer 14, a charge transport layer 16, and an overcoating layer 18. Overcoating layer 18 is formed from a siloxane-phenol composition in accordance with the present disclosure.

It is to be understood herein, that if a "range" or "group" is mentioned with respect to a particular characteristic of the present disclosure, for example, percentage, chemical species, and temperature etc., it relates to and explicitly incorporates herein each and every specific member and combination of sub-ranges or sub-groups therein whatsoever. Thus, any specified range or group is to be understood as a shorthand way of referring to each and every member of a range or group individually as well as each and every possible sub-ranges or sub-groups encompassed therein; and similarly with respect to any sub-ranges or sub-groups therein.

In this regard, disclosed herein is a silane-phenol compound comprising at least two structural moieties. The first moiety is a phenol group and the second moiety is a silane group selected from the group consisting of alkoxysilyl, arylalkoxysilyl, aryloxysilyl, alkylaryloxysilyl, and combination thereof. A phenol group is defined as a hydroxy group that is attached to a monoyclic or polycyclic aromatic hydrocarbon such as benzene or other arene ring. In a variety of exemplary embodiments, the silane-phenol compound of the present disclosure may be represented by the formula (I) as shown below.

$$[HO]_i—A—[D^1—Si(R)_n(OR')_{3-n}]_m \quad (I)$$

in which A is an aromatic group, $D^1$ is a divalent linkage group, R is a hydrogen atom, an alkyl group or an aryl group, R' is an alkyl group having 1 to 5 carbon atoms, n is an integer of from 0 to 2, m is an integer of from 1 to 5, and i is an integer of from 1 to 5.

In formula (I), $D^1$ is selected from one of the following groups:

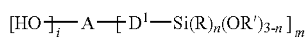

wherein y is an integer of from 1 to about 10,

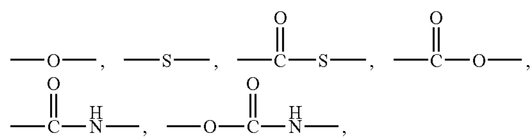

-continued

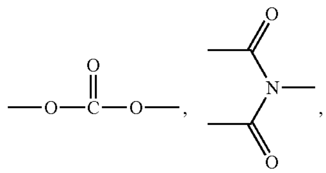

and combination thereof. More specifically, $D^1$ is selected from a group consisting of

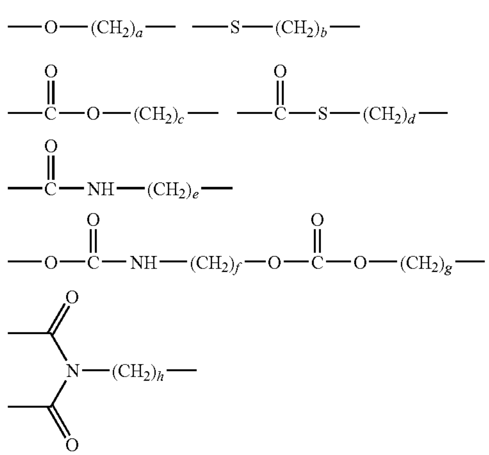

The A group in Formula (I) may include, but are not limited to, the following listed groups:

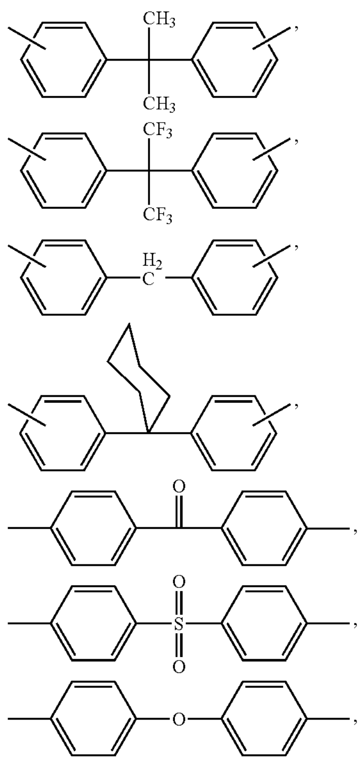

-continued
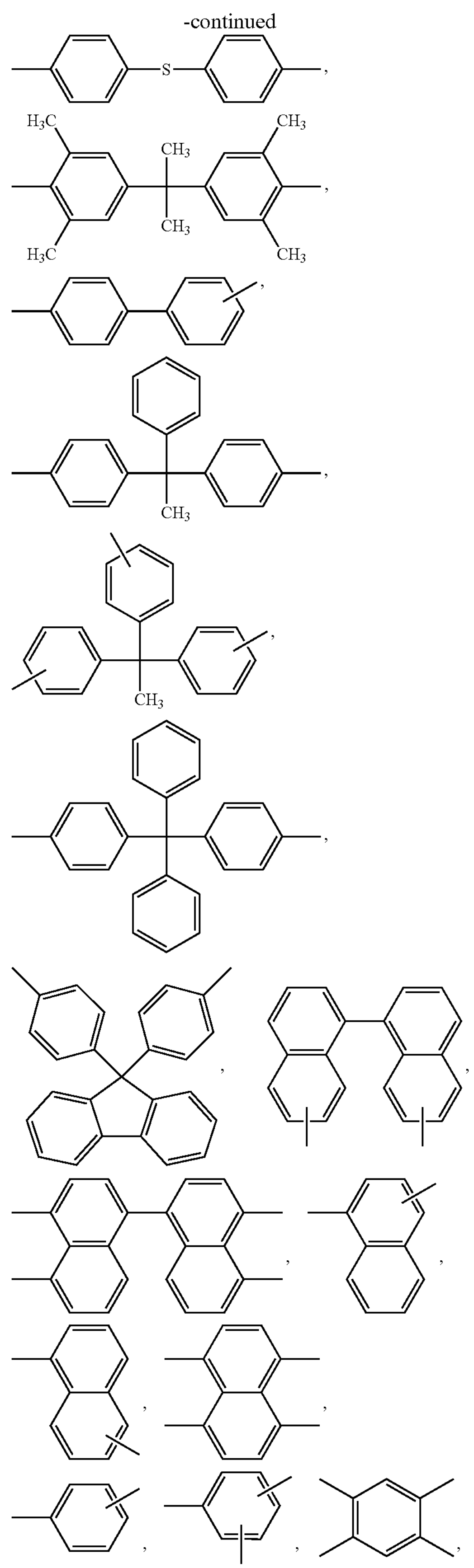
-continued
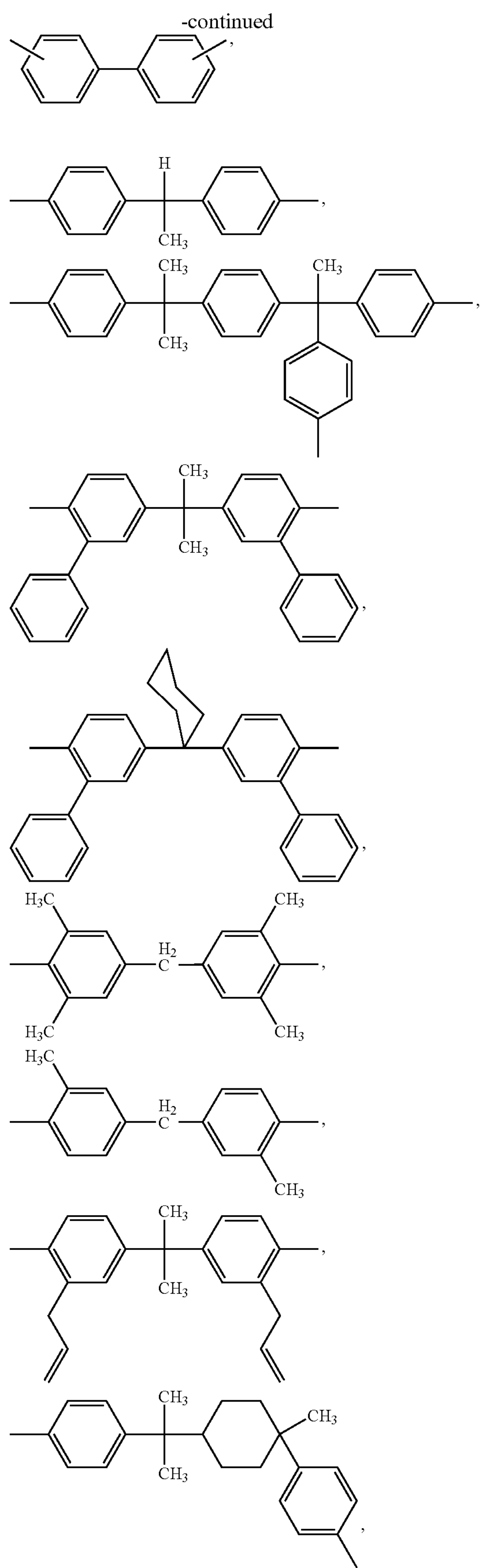

-continued

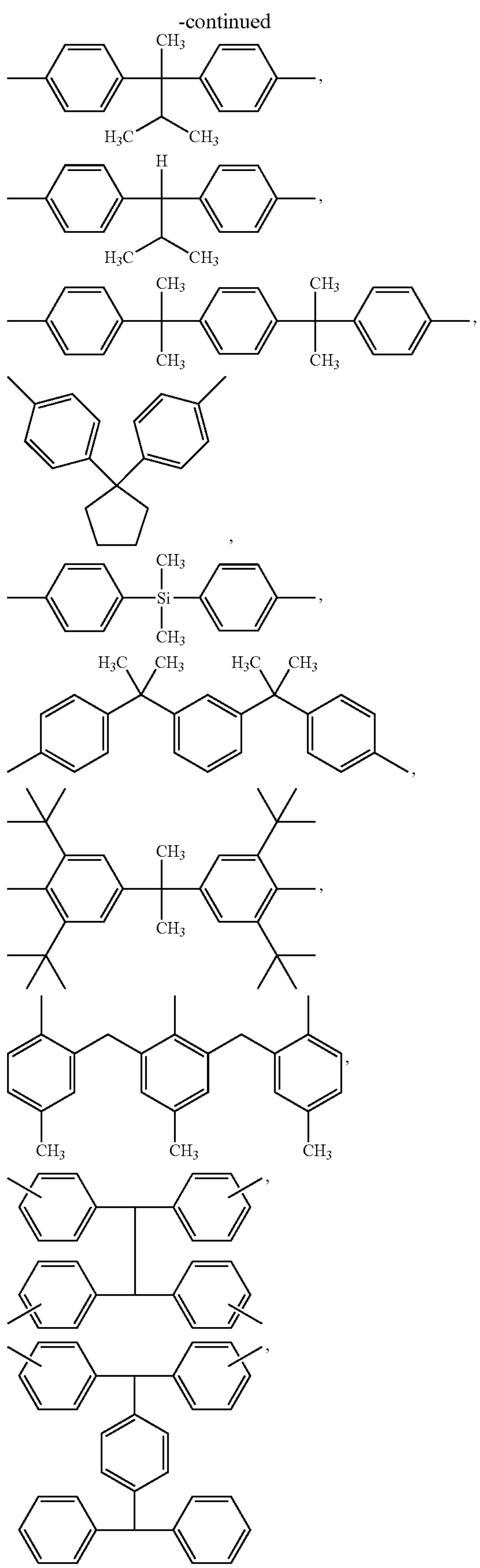

-continued

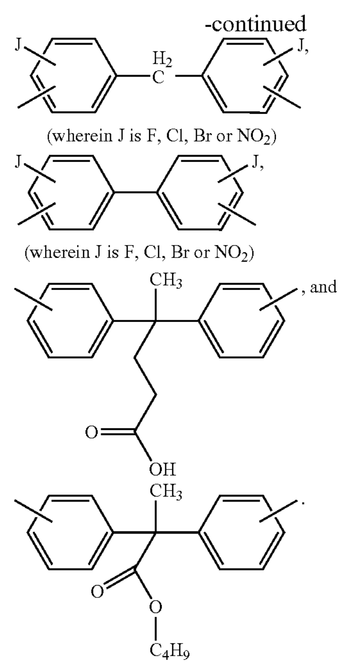

In a specific embodiment, the silane-phenol compound of the present disclosure has a structure of the formula (I-A) as shown below:

(I-A)

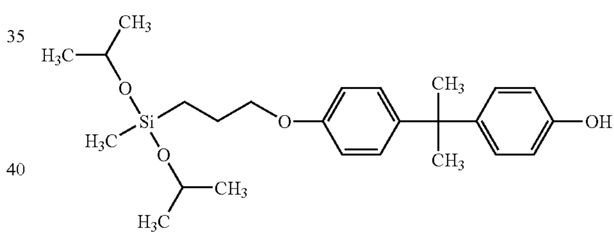

In another specific embodiment, the silane-phenol compound of the present disclosure has a structure of the formula (I-B) as shown below:

(I-B)

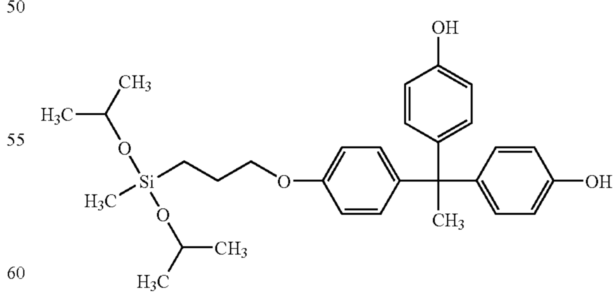

The present disclosure further provides a crosslinked siloxane-phenolic protective overcoat layer comprising the product of hydrolysis and condensation of a silane-phenol compound as previously described and a hydroxymethylated hole transport molecule (HTM). Based on the total weight of the overcoat layer, the amount of the silane-phenol compound present in the overcoat layer in accordance with the present disclosure is from about 10 to about 90 wt %, including from about 20 to about 80 wt %, and from about 30 to about 60 wt %. Based on the total weight of the overcoat layer, the amount of the hydroxymethylated HTM present in the overcoat layer in accordance with the present disclosure may be from about 10 to about 90 wt %, including from about 20 to about 80 wt %, and from about 30 to about 60 wt %.

Generally speaking, the hydroxymethylated hole transport molecule of the present disclosure also comprises at least two structural moieties. The first moiety is any molecular structure that has hole transport capability. The second moiety is a hydroxymethyl group typically substituted on an aromatic structure. For example, the hydroxymethylated HTM compound may be represented by the following formula (II):

$$B{-}[CH_2{-}OH]_i \quad (II)$$

wherein B is an organic group having hole transport capability, i is an integer of from 1 to 5.

Specifically, B group is represented by the following general formula (III)

(III)

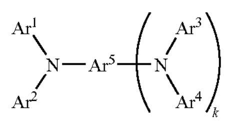

wherein $Ar^1$, $Ar^2$, $Ar^3$ and $Ar^4$ each independently represents a substituted or unsubstituted aryl group, $Ar^5$ represents a substituted or unsubstituted aryl or arylene group, and k represents 0 or 1.

For example, the hydroxymethylated HTM compound may be represented by one of the following formulas:

(II-A)

(II-B)

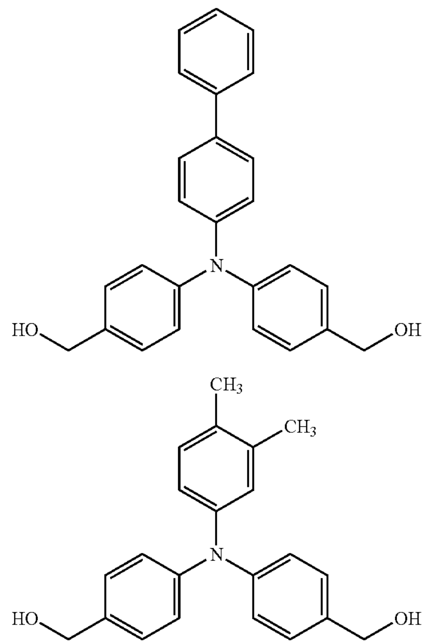

-continued

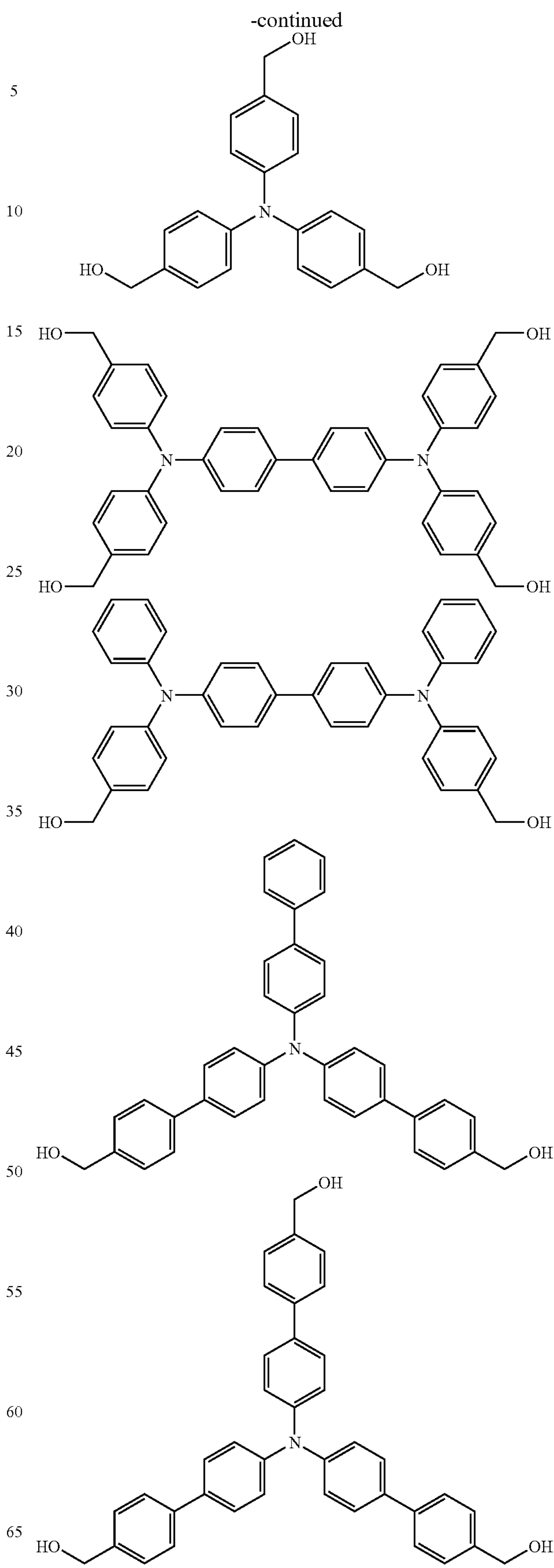

To make a crosslinked siloxane-phenolic protective overcoat layer (OCL), one may cure both the silane and the phenolic type polymer between the phenol functional group and the hydroxymethylated HTM compound to form interpenetrating networks (IPN). In a specific embodiment, the overcoat of the present disclosure comprises the product of hydrolysis of silane functional groups and condensation of two compounds, the hydrolyzed silane-phenol compound with Formula (I-A) and the hydroxymethylated HTM compound with Formula (II-B). After curing, the crosslinked siloxane-phenolic overcoat layer can comprise a structural unit as shown below:

Formula (I-A) compound
Formula (II-B) compound

↓ siloxane-phenolic oligomers

↓

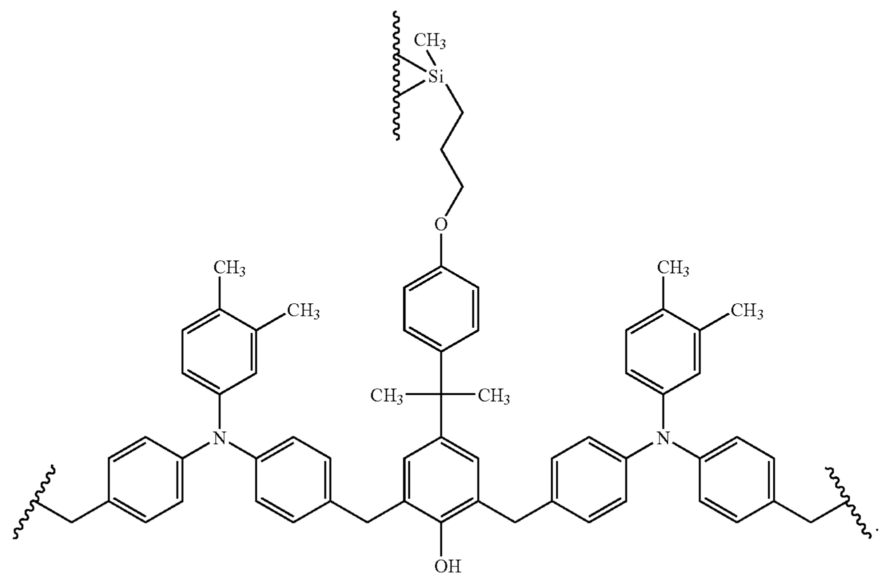

Silocane-phenolic IPN.

In another specific embodiment, the siloxane-phenolic overcoat of the present disclosure comprises the product of hydrolysis of silane functional group and condensation of two compounds, the hydrolyzed silane-phenol compound with Formula (I-B) and the hydroxymethylated HTM compound with Formula (II-A). A crosslinked siloxane-phenolic overcoat can comprise a structural unit as shown below:

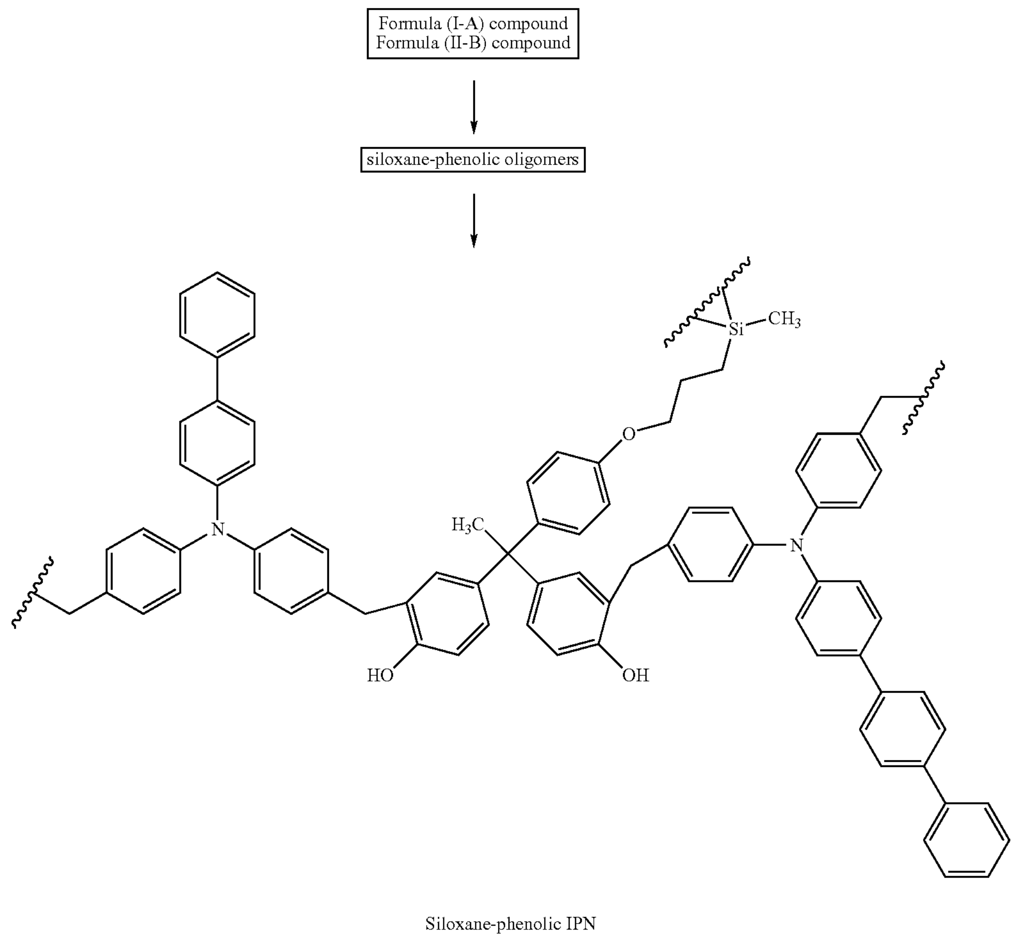

Siloxane-phenolic IPN

The silane-phenol compound may beneficially function as, for example, a matrix binder, in the siloxane-phenolic overcoat of an electrophotographic imaging member such as photoreceptor. Typically, the silane-phenol compound of the present disclosure offers at least two main functions in a siloxane-phenolic overcoat matrix. The silane group is capable of forming silicon network; and a phenol functionality is capable of providing both rigidity and corona-resistance, since, for example, phenol reacts with hydroxymethylated HTM to form phenol-aldehyde type polymer which is known as a high rigidity polymer, in addition, phenol functional group is well-known as good anti-oxidant. Since a crosslinked siloxane-phenolic overcoat layer contains interpenetrating networks of siloxane and phenolic polymer with hole transport and phenol functionalities, it can gain improved properties and performance including deletion resistance such as image deletion resistance, high rigidity for wear and scratch resistance, and anti-oxidation for corona resistance etc.

If desired, the crosslinked siloxane-phenolic overcoat of the present disclosure may further comprise a component selected from the group consisting of a silane coupling agent, a curing catalyst, a stabilizer, a polymer binder, an antioxidant, and mixture thereof.

Optionally, the crosslinked siloxane-phenolic overcoat of the present disclosure may further comprise a silane coupling agent. Based on the total weight of the overcoat, the amount of the silane coupling agent present in the overcoat in accordance with the present disclosure may be from about 0.5 to about 10 wt %, including from about 1 to about 8 wt %, and from about 2 to about 5 wt %.

Exemplary silane coupling agents include, but are not limited to, tetramethoxysilane, vinyltrimethoxysilane, tetraethoxysilane, γ-glycidoxypropyltrimethoxysilane (trade name KBM 403, manufactured by Shin-Etsu Chemical Co., Ltd.), γ-chloropropyltrimethoxysilane, phenyltrimethoxysilane, β-(3,4-epoxycyclohexyl)-ethyltrimethoxysilane, γ-aminopropyltrimethoxysilane, N-β-(aminoethyl)-γ-aminopropylmethylmethoxysilane, N-β-(aminoethyl)-γ-aminopropyltrimethoxysilane, γ-glycidoxypropyltrimethoxysilane, (3,3,3-trifluoropropyl)trimethoxysilane, methyltrimethoxysilane, dimethyldimethoxysilane, diphenyidimethoxysilane, methylphenyldimethoxysilane, γ-aminopropylmethyidimethoxysilane, vinyltriethoxysilane, γ-methacryloxypropyltris(β-methoxyethoxy)silane, 3-(heptafluoroisopropoxy)propyltriethoxysilane, N-β-(aminoethyl)-γ-aminopropyltriethoxysilane, β-aminopropyltriethoxysilane, N,N-bis(β-hydroxyethyl)-γ-aminopropyltriethoxysilane, γ-glycidoxypropyltriethoxysilane, 1H,1H,2H,2H-perfluoroalkyltriethoxysilane, γ-mercaptopropyltrimethoxysilane, 1H,1H,2H,2H-perfluorodecyltriethoxysilane, methyltriethoxysilane, methyltrimethoxyethoxysilane,1H,1H,2H,2H-perfluorooctyltriethoxysilane, (tridecafluoro-1,1,2,2-tetrahydrooctyl)triethoxysilane, γ-glycidoxypropylmethyldiethoxysilane, vinyltriacetoxysilane, and the like.

In various exemplary embodiments, a curing catalyst soluble in the overcoat system, for example, a metal chelate compound, may be used in combination therewith in order to speed up the curing etc. Exemplary metal chelate compounds include, but are not limited to, organic aluminum compound such as aluminum triethylate, aluminum triisopropylate, aluminum tri(sec-butyrate), mono(sec-butoxy) aluminum diisopropylate, diisopropoxyaluminum (ethylacetoacetate), aluminum tris(ethylacetoacetate), aluminum bis (ethylacetoacetate) monoacetylacetonate, aluminum tris (acetylacetonate), aluminum diisopropoxy(acetylacetonate), aluminum isopropoxy-bis(acetylacetonate), aluminum tris (trifluoroacetylacetonate), aluminum tris(hexafluoroacetylacetonate), and the like.

Other exemplary metal chelate compounds include, but are not limited to, organic tin compounds such as dibutyltin dilaurate, dibutyltin dioctylate, and dibutyltin diacetate etc.; organic titanium compounds such as titanium tetrakis(acetylacetonate), titanium bis(butoxy)bis(acetylacetonate) and titanium bis(isopropoxy)bis(acetylacetonate) etc.; and zirconium compounds such as zirconium tetrakis(acetylacetonate), zirconium bis(butoxy)bis(acetylacetonate) and zirconium bis(isopropoxy)bis(acetylace-tonate) etc.

However, from the viewpoints of safety, low cost and long pot life, the organic aluminum compounds are more typically used. In a specific embodiment, the curing catalyst is aluminum tris(acetylacetonate) [$Al(AcAc)_3$]. For example, the amount of the $Al(AcAc)_3$ catalyst present in the crosslinked siloxane-phenolic overcoat layer in accordance with the present disclosure may be from about 0.1 to about 5 wt %, including from about 0.5 to about 3 wt %, and from about 1 to about 2.5 wt %, based on the total weight of solid in the overcoat layer.

When a metal chelate compound such as [$Al(AcAc)_3$] is used, for purpose of improving e.g. pot life and curing efficiency, a stabilizer such as multidentate ligand may be added to the siloxane-phenolic overcoat of the present disclosure. Exemplary multidentate ligands include, but are not limited to, didentate ligands, for example, β-diketone such as acetylacetone, trifluoroacetylacetone, hexafluoroacetylacetone or dipivaloylmethylacetone, an acetoacetate such as methyl acetoacetate and ethyl acetoacetate, bipyridine and derivatives thereof, glycine and derivatives thereof, ethylenediamine and derivatives thereof, 8-oxyquinoline and derivatives thereof, salicylaldehyde and derivatives thereof, catechol and derivatives thereof, and a 2-oxyazo compound; tridentate ligands such as diethyltriamine and derivatives thereof, and nitriloacetic acid and derivatives thereof; and hexadentate ligands such as ethylenediaminetetraacetic acid (EDTA) and derivatives thereof.

In a specific embodiment, the stabilizer is a didentate ligand such as acetylacetone. For example, the amount of the multidentate ligand present in the overcoat in accordance with the present disclosure may be from about 0.1 to about 5 wt %, including from about 0.5 to about 3 wt %, and from about 1 to about 2.5 wt %, based on the total weight of solid in the overcoat.

Typically, the polymer binder that may be used in the crosslinked siloxane-phenolic overcoat of the present disclosure comprises polyvinyl butyral (PVB). The expression "polyvinyl butyral", as employed herein, is defined as a copolymer or terpolymer obtained from the hydrolysis of polyvinyl acetate to form polyvinyl alcohol or a copolymer of polyvinyl alcohol with residual vinyl acetate groups, the resulting polyvinyl alcohol polymer being reacted with butyraldehyde under acidic conditions to form polyvinyl butyral polymers with various amounts of acetate, alcohol and butyraldehyde ketal groups. These polyvinyl butyral polymers are commercially available from, for example, Solutia Inc. with the trade names: BMS, BLS, BL1, B79, B99, and the like. These polymers differ in the amount of acetate, hydroxy, and butyraldehyde ketal groups contained therein. Generally, the weight average molecular weights of polyvinyl butyral vary from about 36,000 to about 98,000. A typical alcohol soluble polyvinyl butyral polymer can be represented by the following formula:

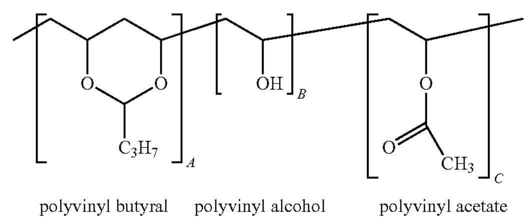

In the above formula, A is a number such that polyvinyl butyral content in the polymer is from about 50 to about 88 mol percent; B is a number such that polyvinyl alcohol content in the polymer is from about 12 to about 50 mol percent; and C is a number such that polyvinyl acetate content in the polymer is from about 0 to about 15 mol percent.

This PVB polymer is the reaction product of a polyvinyl alcohol and butyraldehyde in the presence of a sulphuric acid catalyst. The hydroxyl groups of the polyvinyl alcohol react to give a random butyral structure which can be controlled by varying the reaction temperature and time. The acid catalyst is neutralized with potassium hydroxide. The polyvinyl alcohol is synthesized by hydrolyzing polyvinyl acetate. The resulting hydrolyzed polyvinyl alcohol may contain some polyvinyl acetate moieties. The partially or completely hydrolyzed polyvinyl alcohol is reacted with the butyraldehyde under conditions where some of the hydroxyl groups of the polyvinyl alcohol are reacted, but where some of the other hydroxyl groups of the polyvinyl alcohol remain unreacted. For utilization in the overcoating layer, the reaction product should have a polyvinyl butyral content of from about 50 to about 88 mol percent, a polyvinyl alcohol content of from about 12 mol percent to about 50 mol percent and a polyvinyl acetate content of from about 0 to about 15 mol percent. These PVB polymers are commercially available and include, for example, Butvar B-79 resin (available from Monsanto Chemical Co.) having a polyvinyl butyral content of about 70 mol percent, a polyvinyl alcohol content of 28 mol percent and a polyvinyl acetate content of less than about 2 mol percent, a weight average molecular weight of from about 50,000 to about 80,000; Butvar B-72 resin (available from Monsanto Chemical Co.) having a polyvinyl butyral content of about 56 mol percent by weight, a polyvinyl alcohol content of 42 mol percent and a polyvinyl acetate content of less than about 2 mol percent, a weight average molecular weight of from about 170,000 to about 250,000; and BMS resin (available from Sekisui Chemical) having a polyvinyl butyral content of about 72 mol percent, a vinyl acetate group content of about 5 mol percent, a polyvinyl alcohol content of 23 mol percent and a weight average of molecular weight of about 93,000. Typically, the polyvinyl butyral is present in the final overcoat as tiny spheres. These spheres have an average particle size of from about 0.3 micrometer to about 1 micrometer.

For example, the amount of the polymer binder present in the crosslinked siloxane-phenolic overcoat layer in accordance with the present disclosure may be from about 1 to about 30 wt %, including from about 5 to about 20 wt %, and from about 10 to about 15 wt %, based on the total weight of solid in the overcoat layer.

As a skilled artisan can be aware, deletions of overcoat may sometimes occur due to, for example, the oxidation effects of the corotron or bias charging roll (BCR) effluents that increase the conductivity of the photoreceptor surface. A deletion control agent may be added into the crosslinked siloxane-phenolic overcoat layer to minimize or remove this deletion. A class of deletion control agents includes triphenyl methanes with nitrogen containing substituents such as bis-(2-methyl-4-diethylaminophenyl)-phenylmethane and the like. Other deletion control agents include, for example, hindered phenols such as butylated hydroxy toluene (BHT) and the like. Alcohol soluble deletion control agents can be added directly into, for example, a coating solution.

In a specific embodiment, the deletion control agent is butylated hydroxy toluene (BHT) under commercially available from Aldrich. For example, the amount of the deletion control agent present in the crosslinked siloxane-phenolic overcoat layer in accordance with the present disclosure may be from about 0.1 to about 5 wt %, including from about 0.5 to about 3 wt %, and from about 1 to about 2.5 wt %, based on the total weight of solids in the overcoat.

Any suitable antioxidant may be used in the siloxane-phenolic overcoat of the disclosure. Typically, the antioxidants used comprise a hindered phenol, hindered amine, thioether or phosphite. An antioxidant is effective for improvement of potential stability and image quality in environmental variation.

Exemplary hindered phenol antioxidants include, but are not limited to, Sumilizer BHT-R, Sumilizer MDP-S, Sumilizer BBM-S, Sumilizer WX-R, Sumilizer NW, Sumilizer BP-76, Sumilizer BP-101, Sumilizer GA-80, Sumilizer GM and Sumilizer GS (the above are manufactured by Sumitomo Chemical Co., Ltd.), IRGANOX 1010, IRGANOX 1035, IRGANOX 1076, IRGANOX 1098, IRGANOX 1135, IRGANOX 1141, IRGANOX 1222, IRGANOX 1330, IRGANOX 1425WL, IRGANOX 1520L, IRGANOX 245, IRGANOX 259, IRGANOX 3114, IRGANOX 3790, IRGANOX 5057 and IRGANOX 565 (the above are manufactured by Ciba Specialty Chemicals), and Adecastab AO-20, Adecastab AO-30, Adecastab AO-40, Adecastab AO-50, Adecastab AO-60, Adecastab AO-70, Adecastab AO-80 and Adecastab AO-330 (the above are manufactured by Asahi Denka Co., Ltd.).

Exemplary hindered amine antioxidants include, but are not limited to, Sanol LS2626, Sanol LS765, Sanol LS770, Sanol LS744, Tinuvin 144, Tinuvin 622LD, Mark LA57, Mark LA67, Mark LA62, Mark LA68, Mark LA63 and Sumilizer TPS. Exemplary thioether antioxidants include, but are not limited to, Sumilizer TP-D. Exemplary phosphite antioxidants include, but are not limited to, Mark 2112, Mark PEP 8, Mark PEP 24G, Mark PEP 36, Mark 329K and Mark HP 10 etc.

The amount of the antioxidant present in the crosslinked siloxane-phenolic overcoat in accordance with the present disclosure may be from about 0.1 to about 5 wt %, including from about 0.5 to about 3 wt %, and from about 1 to about 2.5 wt %, based on the total weight of solids in the overcoat layer.

In an embodiment, the crosslinked siloxane-phenolic protective overcoat layer is prepared by curing a sol-gel type materials comprising the product of hydrolysis and condensation of a silane-phenol compound such as the compound of formulas I-A and I-B, and a hydroxymethylated hole transport molecule of the present disclosure such as the compound with formulas (II-A and II-B). The matrix materials in the siloxane overcoat design may also include PVB, BHT, as well as a small amount of curing catalyst Al(AcAc) and stabilizer AcAc etc.

In a specific embodiment, the crosslinked siloxane-phenolic overcoat layer of the present disclosure was prepared by two step process. In the first step, a coating solution was prepared; in the second step the coating solution was coated on a photoreceptor device and cured at an elevated temperature.

In the first step, a coating solution was prepared as follows: (1) methanol exchange of a silane-phenol compound, i.e. the silane-phenol compounds with formulas (I-A) and (I-B) catalyzed with an acid catalyst such as Amerlyst 15 to convert isopropoxysilane group to methoxysilane group in the presence of a hydroxymethylated triarylamine such as the hydroxymethylated HTM with formulas (II-A) and (II-B); (2) polymerization of the silanes to oligomeric siloxanes in 1-butanol in the presence of water; (3) stabilization of the oligomeric siloxanes with AcAc and optionally addition of BXL polymer and curing catalyst $Al(AcAc)_3$.

In the second step, sol-gel chemistry in a siloxane overcoat coating solution of the disclosure affords, after curing at an elevated temperature, for example from about 120° C. to about 150° C., a crosslinked interpenetrating network containing both siloxanes and phenol-aldehyde polymers. The polysiloxanes offer flexibility and toughness to the overcoat allowing good wear and scratch resistance, while phenol-aldehyde polymers grant double functions. One is to provide corona resistance as phenol functional groups are known to act as antioxidants. The other is to increase the rigidity of the overcoat materials and further improve the micromechanical property of the OCL.

Typical alcohol solvents for the coating solution include, but are not limited to, butanol, propanol, isopropanol, ethanol, methanol, and the like, and mixtures thereof. In a specific embodiment, the solvent is 1-butanol and water. The solid content for the coating solution is typically selected from about 5 to 50 wt %, including from about 10 to about 40 wt %, and from about 20 to about 30 wt %, based on the total weight of the coating solution.

The disclosure further provides an electrophotographic imaging member such as photoreceptor, which comprises a crosslinked siloxane-phenolic overcoat layer of the disclosure.

Electrophotographic imaging members may be prepared by any suitable techniques that are well known in the art. Typically, a flexible or rigid substrate is provided with an electrically conductive surface. A charge generating layer is then applied to the electrically conductive surface. A charge blocking layer or undercoat layer may optionally be applied to the electrically conductive surface prior to the application of a charge generating layer, for example, when an organic photoreceptor is to be fabricated. If desired, an adhesive layer may be utilized between the charge blocking layer and the charge generating layer. Usually the charge generation layer is applied onto the blocking layer and a charge transport layer is formed on the charge generation layer. This structure may have the charge generation layer on top of or below the charge transport layer.

The substrate may be opaque or substantially transparent and may comprise any suitable material having the required mechanical properties. Accordingly, the substrate may comprise a layer of an electrically non-conductive or conductive material such as an inorganic or an organic composition. As electrically non-conducting materials, there may be employed various resins known for this purpose including polyesters, polycarbonates, polyamides, polyurethanes, and the like, which are flexible as thin webs. An electrically conducting substrate may be any metal, for example, aluminum, nickel, steel, copper, and the like; or a polymeric material, as described above, filled with an electrically conducting substance, such as carbon, metallic powder, and the like; or an organic electrically conducting material. The electrically insulating or conductive substrate may be in the form of an endless flexible belt, a web, a rigid cylinder, a sheet, and the like.

The thickness of the substrate layer depends on numerous factors, including strength desired and economical considerations. For an electrophotographic imaging member such as a drum, this layer may be of substantial thickness of, for example, up to many centimeters or of a minimum thickness of less than a millimeter. Similarly, a flexible belt may be of substantial thickness, for example, about 250 micrometers, or of minimum thickness less than 50 micrometers, provided there are no adverse effects on the final electrophotographic device.

In embodiments where the substrate layer is not conductive, the surface thereof may be rendered electrically conductive by an electrically conductive coating. The conductive coating may vary in thickness over substantially wide ranges depending upon the optical transparency, degree of flexibility desired, and economic factors. Accordingly, for a flexible photoresponsive imaging device, the thickness of the conductive coating may be including from about 20 angstroms to about 750 angstroms, and from about 100 angstroms to about 200 angstroms for an optimum combination of electrical conductivity, flexibility and light transmission. The flexible conductive coating may be an electrically conductive metal layer formed, for example, on the substrate by any suitable coating technique, such as a vacuum depositing technique or electrodeposition. Typical metals include aluminum, zirconium, niobium, tantalum, vanadium and hafnium, titanium, nickel, stainless steel, chromium, tungsten, molybdenum, and the like.

An optional hole blocking layer or undercoat may be applied to the substrate. Any suitable and conventional blocking layer capable of forming an electronic barrier to holes between the adjacent photoconductive layer and the underlying conductive surface of a substrate may be utilized.

Any suitable adhesive layer well known in the art may optionally be applied to the hole blocking layer or undercoat layer. Typical adhesive layer materials include, for example, polyesters, polyurethanes, and the like. Satisfactory results may be achieved with adhesive layer thickness from about 0.05 micrometer (500 angstroms) to about 0.3 micrometer (3,000 angstroms). Conventional techniques for applying an adhesive layer coating mixture to the charge blocking layer include spraying, dip coating, roll coating, wire wound rod coating, gravure coating, Bird applicator coating, and the like. Drying of the deposited coating may be effected by any suitable conventional technique such as oven drying, infra red radiation drying, air drying and the like.

At least one electrophotographic imaging layer is formed on the adhesive layer, blocking layer or substrate. The electrophotographic imaging layer may be a single layer that performs both charge generating and charge transport functions as is well known in the art or it may comprise multiple layers such as a charge generator layer and charge transport layer.

Charge generator layers may comprise amorphous films of selenium and alloys of selenium and arsenic, tellurium, germanium and the like, hydrogenated amorphous silicon and compounds of silicon and germanium, carbon, oxygen, nitrogen, and the like fabricated by, for example, vacuum evaporation or deposition. The charge generator layers may also comprise inorganic pigments of crystalline selenium and its alloys; Group II-VI compounds; and organic pigments and dyes such as quinacridones, polycyclic pigments such as dibromo anthanthrone pigments, perylene and perinone diamines, polynuclear aromatic quinones, azo pigments including bis-, tris- and tetrakis-azos; quinoline pigments, indigo pigments, thioindigo pigments, bisbenzimidazole pigments, phthalocyanine pigments, quinacridone pigments, lake pigments, azo lake pigments, oxazine pigments, dioxazine pigments, triphenylmethane pigments, azulenium dyes, squalium dyes, pyrylium dyes, triallylmethane dyes, xanthene dyes, thiazine dyes, cyanine dyes, and the like dispersed in a film forming polymeric binder and fabricated by solvent coating techniques.

In an embodiment, phthalocyanines may be employed as photogenerating materials for use in laser printers utilizing infrared exposure systems. Infrared sensitivity is required for photoreceptors exposed to low cost semiconductor laser diode light exposure devices. The absorption spectrum and photosensitivity of the phthalocyanines depend on the central metal atom of the compound. Many metal phthalocyanines have been reported and include, for example, oxyvanadium phthalocyanine, chloroaluminum phthalocyanine, copper phthalocyanine, oxytitanium phthalocyanine, chlorogallium phthalocyanine, hydroxygallium phthalocyanine magnesium phthalocyanine and metal-free phthalocyanine. The phthalocyanines exist in many crystal forms which have a strong influence on photogeneration.

Any suitable polymeric film forming binder material may be employed as the matrix in the charge generating (photogenerating) binder layer. Typical polymeric film forming materials include those described, for example, in U.S. Pat. No. 3,121,006, the entire disclosure of which is incorporated herein by reference. Thus, typical organic polymeric film forming binders include thermoplastic and thermosetting resins such as polycarbonates, polyesters, polyamides, polyurethanes, polystyrenes, polyarylethers, polyarylsulfones, polybutadienes, polysulfones, polyethersulfones, polyethylenes, polypropylenes, polyimides, polymethylpentenes, polyphenylene sulfides, polyvinyl acetate, polysiloxanes, polyacrylates, polyvinyl acetals, polyamides, polyimides, amino resins, phenylene oxide resins, terephthalic acid resins, phenoxy resins, epoxy resins, phenolic resins, polystyrene and acrylonitrile copolymers, polyvinylchloride, vinylchloride and vinyl acetate copolymers, acrylate copolymers, alkyd resins, cellulosic film formers, poly(amideimide), styrene-butadiene copolymers, vinylidenechloride-vinylchloride copolymers, vinylacetate-vinylidenechloride copolymers, styrene-alkyd resins, polyvinylcarbazole, and the like. These polymers may be block, random or alternating copolymers.

A photogenerating composition or pigment may be present in the resinous binder composition in various amounts. Generally, however, from about 5 percent by volume to about 90 percent by volume of the photogenerating pigment is dispersed in about 10 percent by volume to about 95 percent by volume of the resinous binder, and from about 20 percent by volume to about 30 percent by volume of the photogenerating pigment is dispersed in about 70 percent by volume to about 80 percent by volume of the resinous binder composition. The photogenerator layers can also fabricated by vacuum sublimation in which case there is no binder.

Any suitable and conventional technique may be utilized to mix and thereafter apply the photogenerating layer coating mixture. Typical application techniques include spraying, dip coating, roll coating, wire wound rod coating, vacuum sublimation and the like. For some applications, the generator layer may be fabricated in a dot or line pattern. Removing of the solvent of a solvent coated layer may be effected by any suitable conventional technique such as oven drying, infrared radiation drying, air drying and the like.

The charge transport layer may comprise a charge transporting molecule, typically small molecule, dissolved or molecularly dispersed in a film forming electrically inert polymer such as a polycarbonate. The term “dissolved” is defined herein as forming a solution in which the molecules are dissolved in the polymer to form a homogeneous phase. The expression “molecularly dispersed” used herein is defined as a charge transporting small molecule dispersed in the polymer, the small molecules being dispersed in the polymer on a molecular scale.

Any suitable charge transporting or electrically active small molecule may be employed in the charge transport layer of this disclosure. The expression charge transporting “small molecule” is defined herein as a monomer that allows the free charge photogenerated in the transport layer to be transported across the transport layer.

Typical charge transporting molecules include, but are not limited to, pyrene, carbazole, hydrazone, oxazole, oxadiazole, pyrazoline, arylamine, arylmethane, benzidine, thiazole, stilbene and butadiene compounds; pyrazolines such as 1-phenyl-3-(4'-diethylaminostyryl)-5-(4'-diethylamino phenyl)pyrazoline; diamines such as N,N'-diphenyl-N,N'-bis(3-methylphenyl)-(1,1'-biphenyl)-4,4'-diamine; hydrazones such as N-phenyl-N-methyl-3-(9-ethyl)carbazyl hydrazone and 4-diethyl amino benzaldehyde-1,2-diphenyl hydrazone; oxadiazoles such as 2,5-bis (4-N,N'-diethylaminophenyl)-1,2,4-oxadiazole; poly-N-vinylcarbazole, poly-N-vinylcarbazole halide, polyvinyl pyrene, polyvinylanthracene, polyvinylacridine, a pyrene-formaldehyde resin, an ethylcarbazole-formaldehyde resin, a triphenylmethane polymer and polysilane, and the like.

In an embodiment of the present disclosure, to avoid cycle-up in machines with high throughput, the charge transport layer may be substantially free (less than about two percent) of triphenyl methane. As indicated above, suitable electrically active small molecule charge transporting compounds are dissolved or molecularly dispersed in electrically inactive polymeric film forming materials. An exemplary small molecule charge transporting compound that permits injection of holes from the pigment into the charge generating layer with high efficiency and transports them across the charge transport layer with very short transit times is N,N'-diphenyl-N,N'-bis(3-methylphenyl)-(1,1'-biphenyl)-4,4'-diamine. If desired, the charge transport material in the charge transport layer may comprise a polymeric charge transport material or a combination of a small molecule charge transport material and a polymeric charge transport material.

In an embodiment, the charge transport layer may contain an active aromatic diamine molecule, which enables charge transport, dissolved or molecularly dispersed in a film forming binder. The charge transport layer is disclosed in U.S. Pat. No. 4,265,990, the entire disclosure of which is incorporated herein by reference.

Any suitable electrically inactive resin binder insoluble in alcoholic solvent used to apply the overcoat layer may be employed in the charge transport layer. Typical inactive resin binders include polycarbonate resin, polyester, polyarylate, polyacrylate, polyether, polysulfone, and the like. Molecular weights can vary, for example, from about 20,000 to about 150,000. Exemplary binders include polycarbonates such as poly(4,4'-isopropylidene-diphenylene)carbonate (also referred to as bisphenol-A-polycarbonate); polycarbonate; poly(4,4'-cyclohexylidinediphenylene) carbonate (referred to as bisphenol-Z polycarbonate); poly(4,4'-isopropylidene-3,3'-dimethyl-diphenyl)carbonate (also referred to as bisphenol-C-polycarbonate); and the like.

Any suitable charge transporting polymer may also be utilized in the charge transporting layer of this disclosure. The charge transporting polymer should be insoluble in the alcohol solvent employed to apply the overcoat layer. These electrically active charge transporting polymeric materials should be capable of supporting the injection of photogenerated holes from the charge generation material and be incapable of allowing the transport of these holes therethrough.

Any suitable and conventional technique may be utilized to mix and thereafter apply the charge transport layer coating mixture to the charge generating layer. Typical application techniques include spraying, dip coating, roll coating, wire wound rod coating, and the like. Drying of the deposited coating may be effected by any suitable conventional technique such as oven drying, infra red radiation drying, air drying and the like.

Generally, the thickness of the charge transport layer is from about 10 to about 50 micrometers, but thicknesses outside this range can also be used. A hole transport layer should be an insulator to the extent that the electrostatic charge placed on the hole transport layer is not conducted in the absence of illumination at a rate sufficient to prevent formation and retention of an electrostatic latent image thereon. In general, the ratio of the thickness of a hole transport layer to the charge generator layers is typically maintained from about 2:1 to 200:1 and in some instances as great as 400:1. Typically, a charge transport layer is substantially non-absorbing to visible light or radiation in the region of intended use but is electrically “active” in that it allows the injection of photogenerated holes from the photoconductive layer, i.e., charge generation layer, and allows these holes to be transported through itself to selectively, discharge a surface charge on the surface of the active layer.

A protective overcoat layer (OCL) may then be applied onto the charge transport layer. OCL has been shown to increase the mechanical life of an OPC by as much as 10-fold. Crosslinked siloxane-phenolic protective overcoat layers of the present disclosure may be coated on the top of an electrophotographic imaging member such as photoreceptor. Owing to its crosslinked siloxane and phenolic structure, the siloxane-phenolic protective overcoat layer offers excellent abrasive, scratching and marring resistance, among others.

The temperature used for the siloxane crosslinking varies with the specific catalyst and heating time utilized and the degree of crosslinking desired. Generally, the degree of crosslinking selected depends upon the desired flexibility of the final electrophotographic imaging member such as photoreceptor. For example, complete crosslinking may be used for rigid drum or plate photoreceptors. However, partial crosslinking may be desired for flexible photoreceptors having, for example, web or belt configurations. The degree of crosslinking can be controlled by the relative amount of catalyst employed.

The thickness of the crosslinked siloxane-phenolic protective overcoat layer of the present disclosure depends upon the abrasiveness of the charging (e.g., bias charging roll), cleaning (e.g., blade or web), development (e.g., brush), transfer (e.g., bias transfer roll), etc., in the electrophotographic imaging system employed. Generally, the overcoat layer thickness may range up to about 10 micrometers. A typical thickness is from about 1 micrometer to about 5 micrometers.

Any suitable and conventional technique may be utilized to mix and thereafter apply the overcoat layer coating mixture to the charge generating layer. Typical application techniques include spraying, dip coating, roll coating, wire wound rod coating, and the like. Drying of the deposited coating may be effected by any suitable conventional technique such as oven drying, infrared radiation drying, air drying and the like.

The dried overcoating should transport holes during imaging and should not have too high free carrier concentration. Free carrier concentration in an overcoat increases the dark decay. It is desirable that the dark decay of the overcoated layer is about the same as, or is close to, that of an unovercoated counterpart.

The electrophotographic imaging member such as photoreceptor according to the present disclosure may be incorporated into various imaging systems such as those conventionally known as xerographic imaging devices or electrophotographic image forming devices. Additionally, the imaging members may be selected for imaging and printing systems with visible, near-red and/or infrared light. In this embodiment, the imaging members may be negatively or positively charged, exposed to light having a wavelength of from about 700 to about 900, such as generated by solid state layers, e.g., arsenide-type lasers, either sequentially or simultaneously, followed by developing the resulting image and transferring it to a print substrate such as transparency or paper. Additionally, the imaging members may be selected for imaging and printing systems with visible light. In this embodiment, the imaging members may be negatively or positively charged, exposed to light having a wavelength of from about 400 to about 700 nanometers, followed by development with a known toner, and then transferring and fixing of the image on a print substrate.

In an embodiment, an electrophotographic image forming device may comprise the electrophotographic imaging member as discussed above, a charging device, an electrostatic image forming station, an image developing station, and an image transfer station.

In an embodiment, the electrophotographic image forming device may be used to generate images with the electrophotographic imaging member such as photoreceptor disclosed herein. Generally, the imaging member may be first charged with a corona charging device such as a corotron, dicorotron, scorotron, pin charging device, bias charging roll (BCR) or the like. Then, an electrostatic image is generated on the imaging member with an electrostatic image forming device. Subsequently, the electrostatic image is developed by known developing devices at one or more developing stations that apply developer compositions such as, for example, compositions comprised of resin particles, pigment particles, additives including charge control agents and carrier particles, etc., reference being made to, for example, U.S. Pat. Nos. 4,558,108; 4,560,535; 3,590,000; 4,264,672; 3,900,588 and 3,849,182, the disclosures of each of these patents being totally incorporated herein by reference. The developed electrostatic image is then transferred to a suitable print substrate such as paper or transparency at an image transfer station, and affixed to the substrate. Development of the image may be achieved by a number of methods, such as cascade, touchdown, powder cloud, magnetic brush, and the like.

Transfer of the developed image to a print substrate may be by any suitable method, including those wherein a corotron or a biased roll is selected. The fixing step may be performed by means of any suitable method, such as flash fusing, heat fusing, pressure fusing, vapor fusing, and the like.

Following transfer of the developed image from the imaging member surface, the imaging member may be cleaned of any residual developer remaining on the surface, and also cleaned of any residual electrostatic charge prior to being subjected to charging for development of a further or next image.

Specific embodiments of the disclosure will now be described in detail. These examples are intended to be illustrative, and the disclosure is not limited to the materials, conditions, or process parameters set forth in these embodiments. All parts and percentages are by weight unless otherwise indicated.

EXAMPLE 1

Preparation of the Silane-Phenol Compound with Formula (I-A)

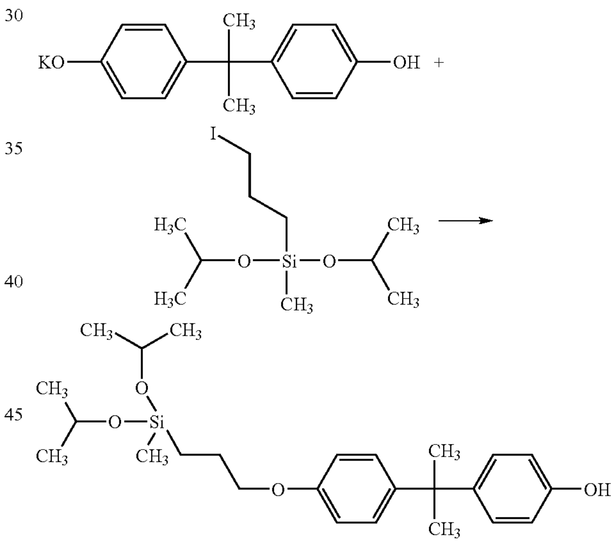

Bisphenol A (BPA) (22.83 g) was dissolved in isopropanol (100 mL) in a 500 mL round-bottomed flask. To the solution was added a solution of 20 wt % of potassium isopropoxide in isopropanol (49 g) through a dropping funnel. After addition, the solution was stirred at room temperature for 3 hours and the excess isopropanol was removed by rotary evaporation. The remaining solid was dissolved in dimethylformamide (DMF) (100 mL). To the solution was added iodopropyldiisoproxymethylsilane (36.33 g) and the temperature was maintained at about 70° C. for an hour, then cooled to 25° C. Potassium iodide (21 g) was added into the solution and it was stirred for about an hour. Hexane (300 mL) was added to extract the bis-silane by product. Then, cyclohexane (300 mL) containing 10% toluene was added to extract the product. The organic layer was collected and washed with deionized water and brine, and dried over sodium sulfate. The excess solvent was removed by rotary evaporation and the final product was purified by distillation at 180° C. under reduced pressure. The yield of compound (III) was 8.5 g (37%). The desired structure of the product was confirmed by $^{1}H$ NMR spectroscopy.

EXAMPLE 2

Preparation of the Silane-Phenol Compound with Formula (I-B)

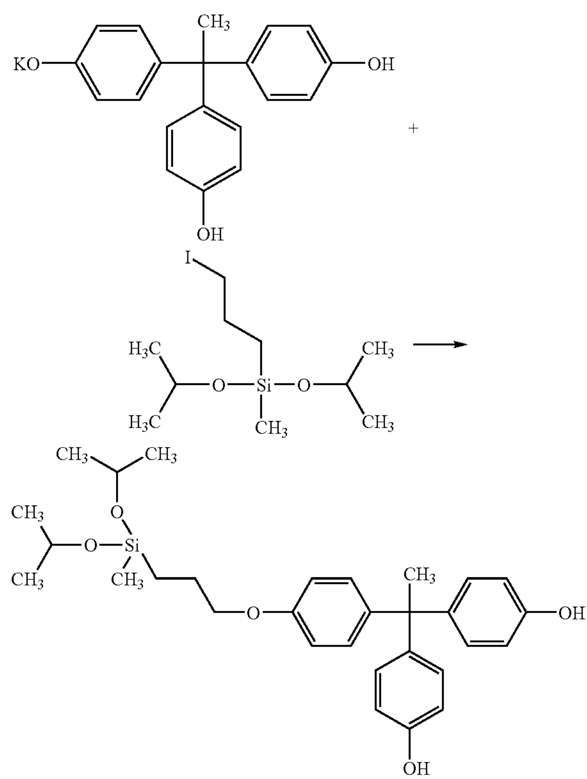

Tris(hydroxyphenyl)ethane (11.54 g) was dissolved in isopropanol (100 mL) in a 500 mL round-bottomed flask. To the solution was added a solution of 20 wt % of potassium isopropoxide in isopropanol (18.49 g) through a dropping funnel. After addition, the solution was stirred at room temperature for 3 hours and the excess isopropanol was removed by rotary evaporation. The remaining solid was dissolved in dimethylformamide (DMF) (150 mL). To the solution was added iodopropyldiisoproxymethylsilane (16.17 g) and the temperature was maintained at about 70° C. for an hour, then cooled to 25° C. Potassium iodide (10 g) was added into the solution and it was stirred for about 4 hour. Hexane (300 mL) was added to extract the tri-silane by product. Then, cyclohexane (300 mL) was added to extract the bis-silane product. Finally, toluene (400 mL) was used to extract the product. The toluene layer was collected and washed with deionized water and brine, and dried over sodium sulfate. The excess solvent was removed by rotary evaporation and the final product was purified by flush column chromatography. The yield of compound (I-B) was 12.1 g (63%). The desired structure of the product was confirmed by $^{1}H$ NMR spectroscopy.

COMPARATIVE EXAMPLE

A conventional crosslinked siloxane overcoat is prepared, i.e., without the silane-phenol compound.

Specifically, 2.75 parts of a silanized hole transport molecule, 1.45 parts of binder material 1,6-bis(dimethoxymethylsilyl)-hexane, and 2.75 parts of methanol are mixed, and 0.5 parts of an ion exchange resin (AMBERLIST H15) are added thereto, followed by stirring for 2 hours. Furthermore, 8 parts of butanol and 1.23 parts of distilled water are added to this mixture, followed by stirring at room temperature for 30 minutes. Then, the resulting mixture is filtered to remove the ion exchange resin, and 0.045 parts of aluminum trisacetylacetonate ($Al(AcAc)_3$), 0.045 parts of acetylacetone (AcAc), 2 parts of a polyvinyl butyral resin (trade name: S-LEC KW-1, manufactured by Sekisui Chemical Co., Ltd.), 0.045 parts of butylated-hydroxytoluene (BHT) and 0.065 parts of a hindered phenol antioxidant (IRGANOX 259) are added to a filtrate obtained, and thoroughly dissolved therein for 2 hours to obtain a coating solution for a protective layer.

This coating solution is applied onto a charge transfer layer by dip coating (coating speed: about 170 mm/min), and dried by heating at 130° C. for one hour to form the protective layer having a film thickness of 3 μm, thereby obtaining a desired electrophotographic photoreceptor.

EXAMPLE 3

Siloxane-Phenolic Overcoat Coating Solution Preparation

The silane-phenol compound with formula I-A (0.5 g) and the hydroxymethylated triarylamine with formula II-B (0.5 g) were mixed with 1.5 g of methanol in the presence of 0.1 g of Amerlyst 15. The mixture was shaken for about 2-3 hours, then was added 2.5 g of 1-butanol and 0.3 g of water. The resulting mixture was shaken for 30 minutes and decanted into a bottle containing 0.01 g of AcAc, 0.01 g of $Al(AcAc)_3$, and 0.01 g BHT left Amerlyst out. The resulting solution was shaken for 2 hours and filtered through 0.45 μm PTFE filter, then subjected to coating.

EXAMPLE 4

The Siloxane-Phenolic Overcoat Coating Solution Preparation

The silane-phenol compound with formula I-B (2.2 g), the hydroxymethylated triarylamine molecule with formula II-B (2.5 g) were mixed with 2.75 g of methanol in the presence of 0.5 g of Amerlyst 15. The mixture was shaken for about 2-3 hours, then was added 8 g of 1-butanol and 2 g of water. The resulting mixture was shaken for 30 minutes and decanted into a bottle containing 0.25 g of AcAc, 0.25 g of $Al(AcAc)_3$, 0.25 g BHT and 0.75 g of BXL polymer left Amerlyst 15 out. The resulting solution was shaken for 2 hours and filtered through 0.45 μm PTFE filter, then subjected to coating.

EXAMPLE 5

A Photoreceptor Drum Preparation

A titanium oxide/phenolic resin dispersion was prepared by ball milling 15 grams of titanium dioxide (STR60N™, Sakai Company), 20 grams of the phenolic resin (VARCUM™ 29159, OxyChem Company, $M_w$ about 3,600, viscosity about 200 cps) in 7.5 grams of 1-butanol and 7.5 grams of xylene with 120 grams of 1 millimeter diameter sized $ZrO_2$ beads for 5 days. Separately, a slurry of $SiO_2$ and a phenolic resin was prepared by adding 10 grams of $SiO_2$ (P100, Esprit) and 3 grams of the above phenolic resin into 19.5 grams of 1-butanol and 19.5 grams of xylene. The resulting titanium dioxide dispersion was filtered with a 20 micrometer pore size nylon cloth, and then the filtrate was measured with Horiba Capa 700 Particle Size Analyzer, and there was obtained a median $TiO_2$ particle size of 50 nanometers in diameter and a $TiO_2$ particle surface area of 30 $m^2$/gram with reference to the above $TiO_2$/VARCUM dispersion. Additional solvents of 5 grams of 1-butanol, and 5 grams of xylene; 2.6 grams of bisphenol S (4,4'-sulfonyidiphenol), and 5.4 grams of the above prepared $SiO_2$/VARCUM slurry were added to 50 grams of the above resulting titanium dioxide/VARCUM dispersion, referred to as the coating dispersion. Then the aluminum drum, cleaned with detergent and rinsed with de-ionized water, was dip coated with the coating dispersion at a pull rate of 160 millimeters/minute, and subsequently, dried at 160° C. for 15 minutes, which resulted in an undercoat layer (UCL) comprised of $TiO_2$/$SiO_2$/VARCUM/bisphenol S with a weight ratio of about 52.7/3.6/34.5/9.2 and a thickness of 3.5 microns.

A 0.5 micron thick photogenerating layer was subsequently dip coated on top of the above generated undercoat layer from a dispersion of Type V hydroxygallium phthalocyanine (12 parts), alkylhydroxy gallium phthalocyanine (3 parts), and a vinyl chloride/vinyl acetate copolymer, VMCH ($M_n$=27,000, about 86 weight percent of vinyl chloride, about 13 weight percent of vinyl acetate and about 1 weight percent of maleic acid) available from Dow Chemical (10 parts), in 475 parts of n-butylacetate.

Subsequently, a 24 μm thick charge transport layer (CTL) was dip coated on top of the photogenerating layer from a solution of N,N'-diphenyl-N,N-bis(3-methylphenyl)-1,1'-biphenyl-4,4'-diamine (82.3 parts), 2.1 parts of 2,6-Di-tert-butyl-4methylphenol (BHT) from Aldrich and a polycarbonate, PCZ-400 [poly(4,4'-dihydroxy-diphenyl-1-1-cyclohexane), $M_w$=40,000] available from Mitsubishi Gas Chemical Company, Ltd. (123.5 parts) in a mixture of 546 parts of tetrahydrofuran (THF) and 234 parts of monochlorobenzene. The CTL was dried at 115° C. for 60 minutes.

EXAMPLE 6

A Flexible Belt Photoreceptor Preparation

On a 75 micron thick titanized MYLAR® substrate was coated by draw bar technique a barrier layer formed from hydrolyzed gamma aminopropyltriethoxysilane having a thickness of 0.005 micron. The barrier layer coating composition was prepared by mixing 3-aminopropyltriethoxysilane with ethanol in a 1:50 volume ratio. The coating was allowed to dry for 5 minutes at room temperature, followed by curing for 10 minutes at 110° C. in a forced air oven. On top of the blocking layer was coated a 0.05 micron thick adhesive layer prepared from a solution of 2 weight percent of a DuPont 49K (49,000) polyester in dichloromethane. A 0.2 micron photogenerating layer was then coated on top of the adhesive layer with a wire wound rod from a dispersion of hydroxy gallium phthalocyanine Type V (22 parts) and a vinyl chloride/vinyl acetate copolymer, VMCH ($M_n$=27,000, about 86 weight percent of vinyl chloride, about 13 weight percent of vinyl acetate and about 1 weight percent of maleic acid) available from Dow Chemical (18 parts), in 960 parts of n-butylacetate, followed by drying at 100° C. for 10 minutes. Subsequently, a 24 μm thick charge transport layer (CTL) was coated on top of the photogenerating layer by a draw bar from a solution of N,N'-diphenyl-N,N-bis(3-methylphenyl)-1,1'-biphenyl4,4'-diamine (67.8 parts), 1.7 parts of 2,6-Di-tert-butyl-4methylphenol (BHT) from Aldrich and a polycarbonate, PCZ-400 [poly(4,4'-dihydroxy-diphenyl-1-1-cyclohexane), $M_w$=40,000] available from Mitsubishi Gas Chemical Company, Ltd. (102 parts) in a mixture of 410 parts of tetrahydrofuran (THF) and 410 parts of monochlorobenzene. The CTL was dried at 115° C. for 60 minutes.

EXAMPLE 7 AND 8

Crosslinked Siloxane-Phenolic Overcoat Coating and Evaluation

The coating solutions of Example 3 and 4 were applied onto photoreceptors with the same coating technique and parameters as described in Comparative Example.

The photoreceptors prepared in Comparative Example, Examples 2 and 3 were tested for photoreceptor device evaluation. Specifically, the photoreceptors were tested for their electrical characteristics ($V_{high}$ and $V_{low}$), wear rate, and deletion resistance.

The electrical evaluation and wear testing and printing test of photoreceptors were performed by the following procedure:

The xerographic electrical properties of the above prepared photoconductive imaging member and other similar members can be determined by known means, including electrostatically charging the surfaces thereof with a corona discharge source until the surface potentials, as measured by a capacitively coupled probe attached to an electrometer, attained an initial value Vo of about −800 volts. After resting for 0.5 second in the dark, the charged members attained a surface potential of Vddp, dark development potential. Each member was then exposed to light from a filtered Xenon lamp thereby inducing a photodischarge which resulted in a reduction of surface potential to a Vbg value, background potential. The percent of photodischarge was calculated as 100×(Vddp−Vbg)/Vddp. The desired wavelength and energy of the exposed light was determined by the type of filters placed in front of the lamp. The monochromatic light photosensitivity was determined using a narrow band-pass filter. The photosensitivity of the imaging member is usually provided in terms of the amount of exposure energy in ergs/$cm^2$, designated as $E_{1/2}$, required to achieve 50 percent photodischarge from Vddp to half of its initial value. The higher the photosensitivity, the smaller is the $E_{1/2}$ value. The $E_{7/8}$ value corresponds to the exposure energy required to achieve ⅞ photodischarge from Vddp. The device was finally exposed to an erase lamp of appropriate light intensity and any residual potential (Vresidual) was measured. The imaging members were tested with an monochromatic light exposure at a wavelength of 780±10 nanometers and an erase light with the wavelength of 600 to 800 nanometers and intensity of 200 ergs·$cm^2$.

The devices were then mounted on a wear test fixture to determine the mechanical wear characteristics of each device. Photoreceptor wear was determined by the change in thickness of the photoreceptor before and after the wear test. The thickness was measured, using a permascope at one-inch intervals from the top edge of the coating along its length using a permascope, ECT-100. All of the recorded thickness values are averaged to obtain the average thickness of the entire photoreceptor device. For the wear test the photoreceptor was wrapped around a drum and rotated at a speed of 140 rpm. A polymeric cleaning blade is brought into contact with the photoreceptor at an angle of 20 degrees and a force of approximately 60-80 grams/cm. Single component toner is trickled on the photoreceptor at rate of 200 mg/min. The drum is rotated for 150 kcycle during a single test. The wear rate is equal to the change in thickness before and after the wear test divided by the # of kcycles.

Immediately after electrical cycling, the electrophotographic photoreceptors of each of Examples 10-14 and Comparative Examples 1 were placed in a xerographic customer replaceable unit (CRU), as is used in a DOCUCOLOR 1632 (manufactured by Xerox Corporation) and placed in such a machine for print testing.

Then, print tests were carried out on each photoreceptor. The tests were carried out under the same conditions of high temperature and high humidity (28° C. and 85% relative humidity), and the initial image quality and surface state of the electrophotographic photoreceptors and the image quality and surface state of the electrophotographic photoreceptors after 5,000 prints were determined.

The results show that the photoreceptor exhibit comparable electrical characteristics and wear rate, but the photoreceptors of Examples 3 and 4 exhibits significant improvement in image deletion resistance and cleanability as compared to the photoreceptor of Comparative Example 1 (Table 1).

TABLE I

| | | Image quality (initial) | | | Image quality (after 5,000 prints) | | |
|---|---|---|---|---|---|---|---|
| | cleanability | Good | medium | poor | Good | medium | poor |
| Comparative Example 1 | poor | | | ✓ | | | ✓ |
| Example 3 | good | ✓ | | | ✓ | | |
| Example 4 | good | ✓ | | | ✓ | | |

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. An electrophotographic imaging member comprising:

a charge generating layer, a charge transport layer, and an outermost protective layer comprising a product formed by crosslinking at least one siloxane-phenol compound with at least one hydroxymethylated hole transport molecule;

wherein the at least one silane-phenol compound is represented by the formula (I) as shown below:

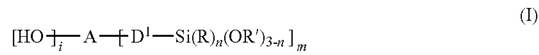

$$[HO]_i—A—[D^1—Si(R)_n(OR')_{3-n}]_m \quad (I)$$

in which A is an aromatic group, $D^1$ is a divalent linkage group, R is a hydrogen atom, an alkyl group or an aryl group, R' is an alkyl group having 1 to 5 carbon atoms, n is an integer of from 0 to 2, m is an integer of from 1 to 5, and i is an integer of from 1 to 5; and wherein the hydroxymethylated hole transport molecule is of formula (II)

$$B—[CH_2—OH]_i \quad (II)$$

wherein B is an organic group having hole transport capability, and i is an integer of from 1 to 5.

2. The electrophotographic imaging member according to claim 1, wherein said B group is represented by the following general formula (III)

$$\begin{matrix} Ar^1 \\ & N—Ar^5—\left( N \begin{matrix} Ar^3 \\ Ar^4 \end{matrix} \right)_k \\ Ar^2 \end{matrix} \quad (III)$$

wherein $Ar^1$, $Ar^2$, $Ar^3$ and $Ar^4$ each independently represents a substituted or unsubstituted aryl group, $Ar^5$ represents a substituted or unsubstituted aryl or arylene group, and k represents 0 or 1.

3. The electrophotographic imaging member according to claim 1, wherein the at least one hydroxymethylated hole transport molecule is selected from the group consisting of (II-A)

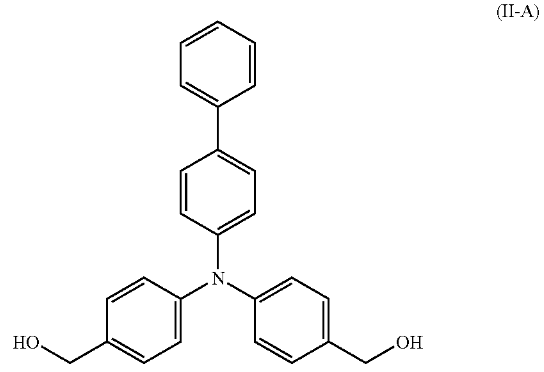

(II-B)

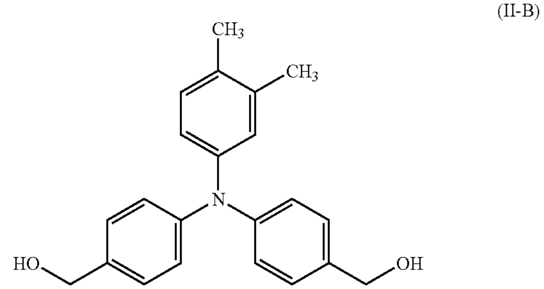

-continued

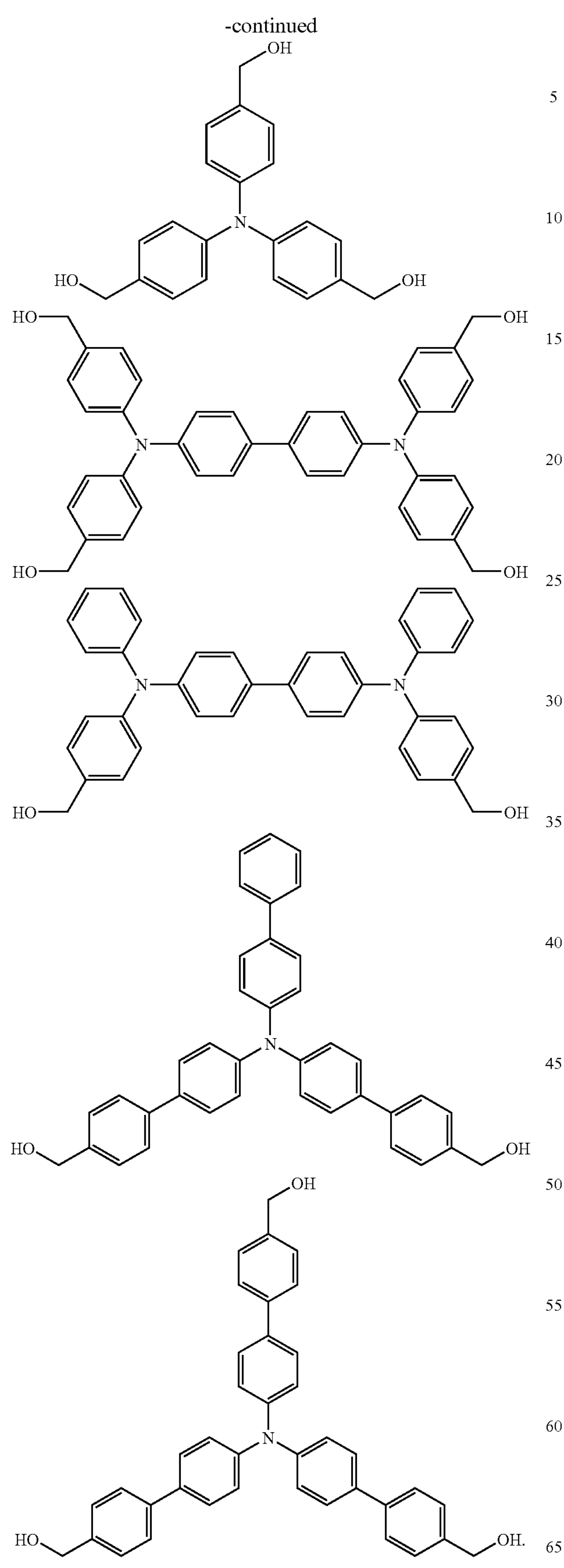

4. The electrophotographic imaging member in according to claim 1, wherein the amount of the product formed by crosslinking the at least one silane-phenol compound with the at least one hydroxymethylated hole transport molecule is from about 20 to about 80 wt %, based on the total weight of all components in the outermost protective layer.

5. The electrophotographic imaging member in according to claim 1, wherein the amount of the hydroxymethylated hole transport compound is from about 20 to about 80 wt %, based on the total weight of all components in the outermost protective layer.

6. The imaging member according to claim 1, in which the A group of the silane-phenol compound is selected from one of the following multiple-valent aryl groups:

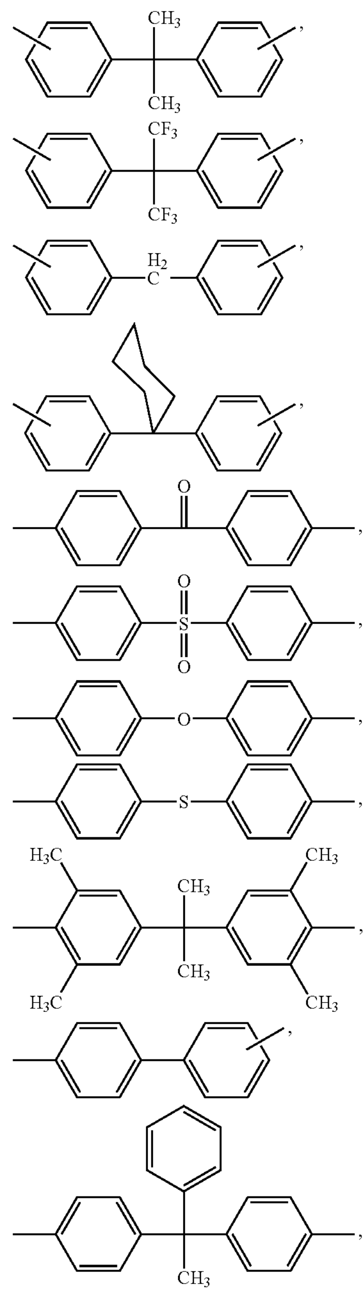

-continued
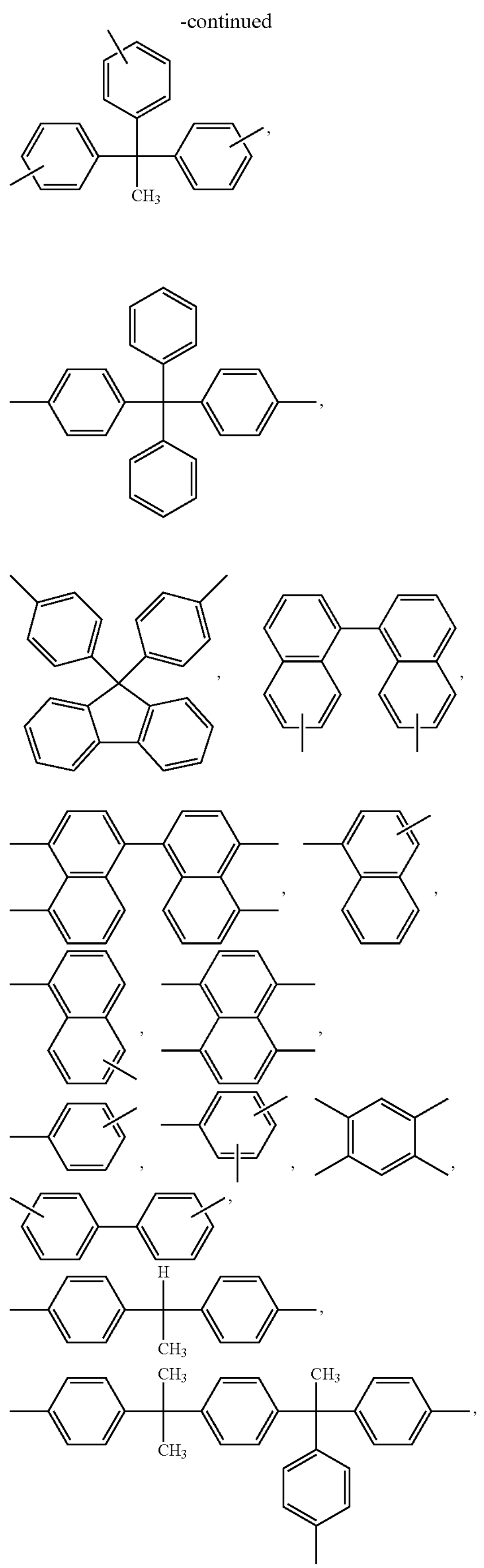
-continued
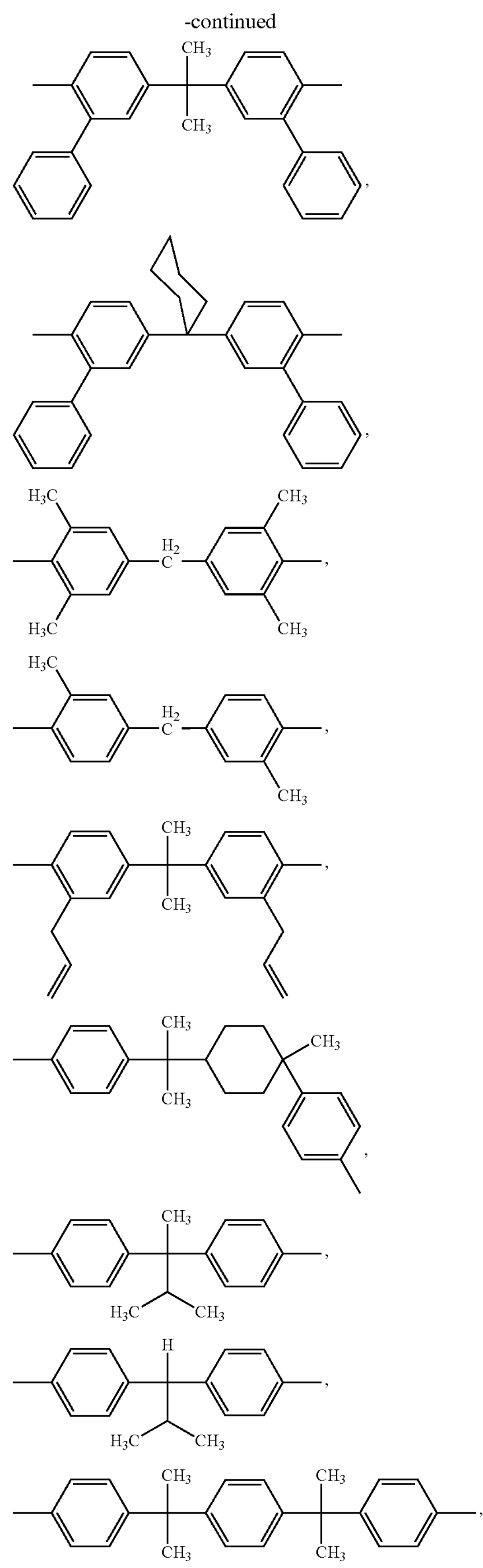

-continued
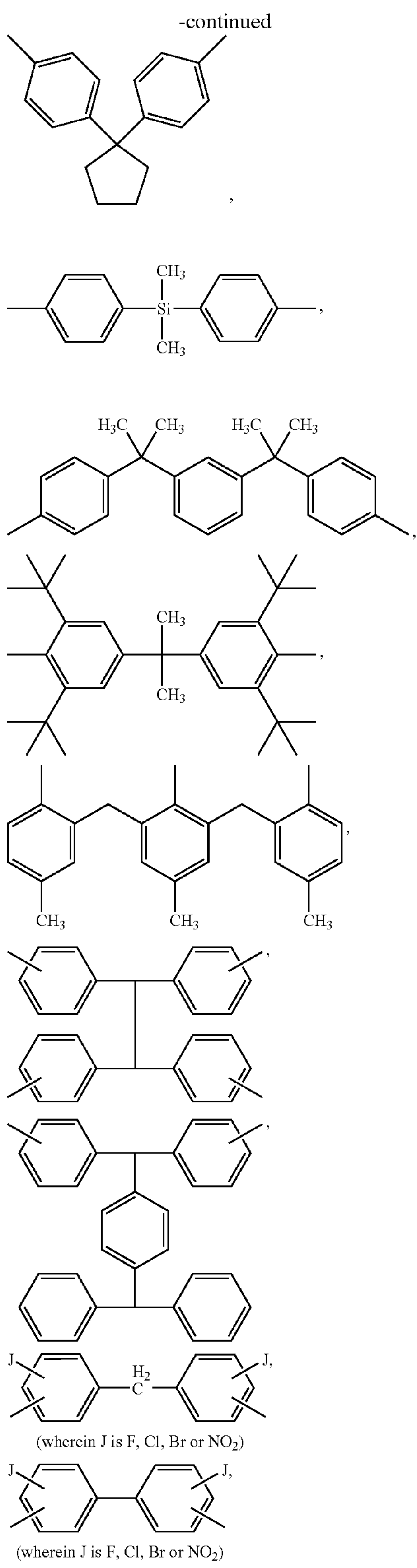
-continued
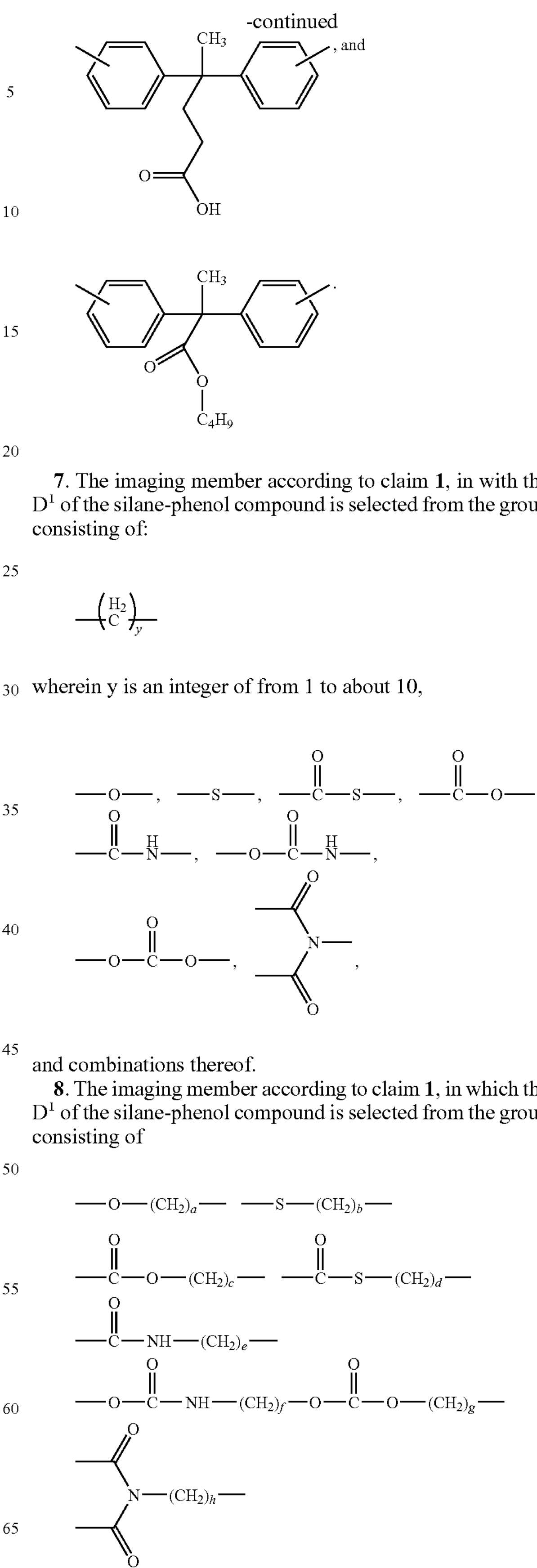
7. The imaging member according to claim 1, in with the $D^1$ of the silane-phenol compound is selected from the group consisting of:
wherein y is an integer of from 1 to about 10,
and combinations thereof.
8. The imaging member according to claim 1, in which the $D^1$ of the silane-phenol compound is selected from the group consisting of wherein a though h are independently an integer from of from 1 to about 10.

9. The imaging member according to claim 1, wherein the silane-phenol compound is represented by one of the formulas as shown below:

(IA)

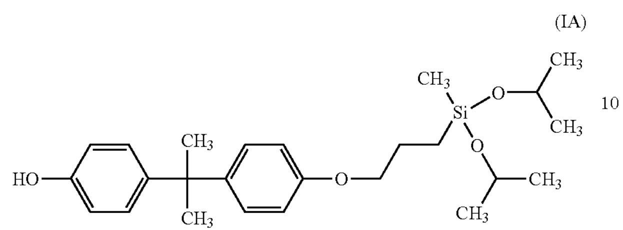

(IB)

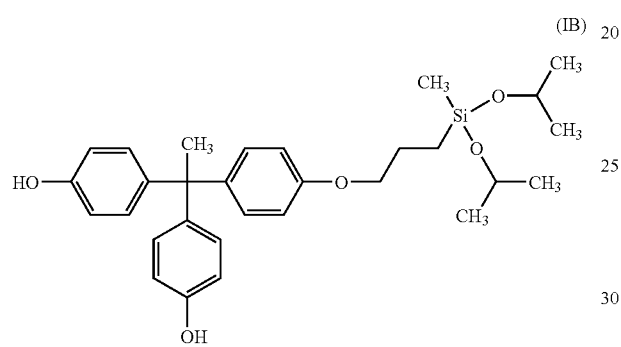

(IC)

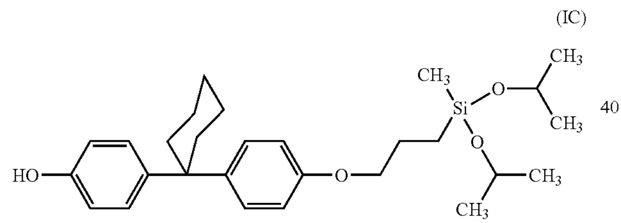

(ID)

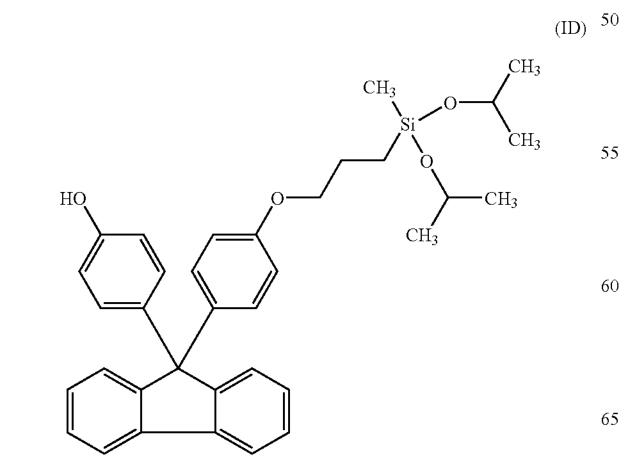

-continued (IE)

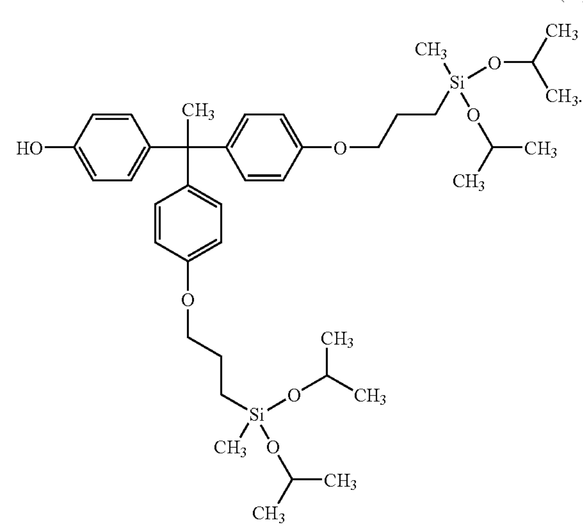

10. The electrophotographic imaging member according to claim 1, wherein the at least one hydroxymethylated hole transport molecule is selected from the group consisting of formulas (II-A) and (II-B):

(II-A)

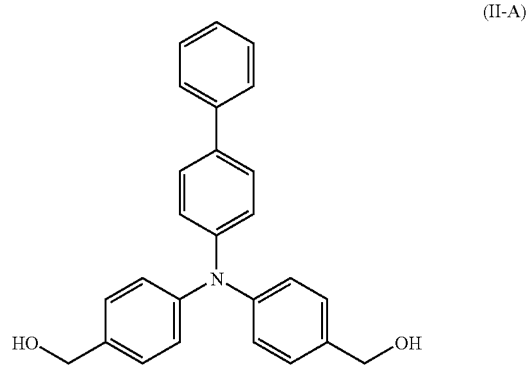

(II-B)

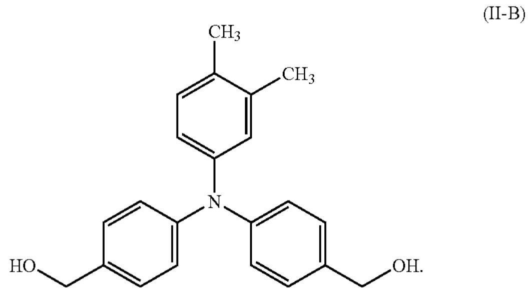

11. The electrophotographic imaging member according to claim 1, wherein the crosslinked siloxane-phenolic outermost protective layer comprises both siloxane and phenol-aldehyde condensates.

12. The electrophotographic imaging member according to claim 11, wherein the crosslinked siloxane-phenolic outermost protective layer comprises a structural unit as shown below:

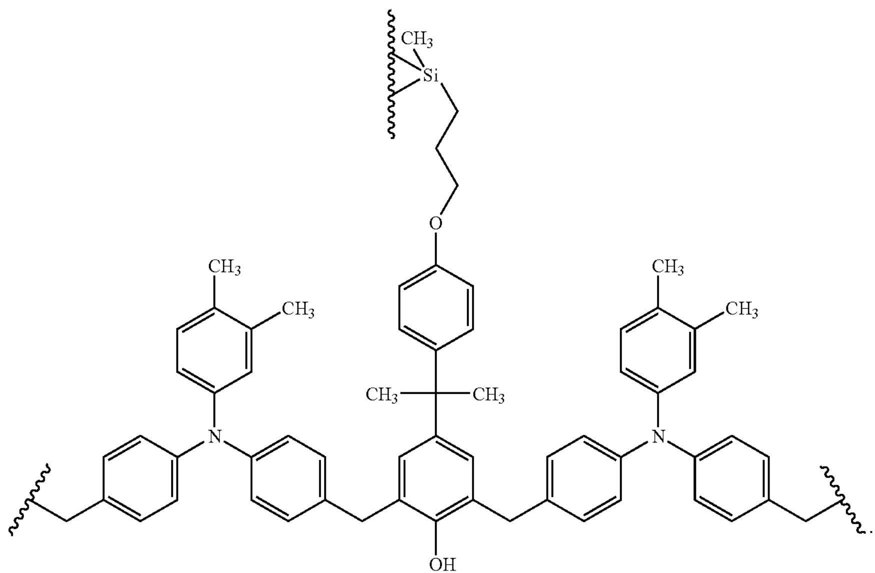

13. The electrophotographic imaging member according to claim 11, wherein the crosslinked siloxane-phenolic outermost protective layer comprises a structural unit as shown below:

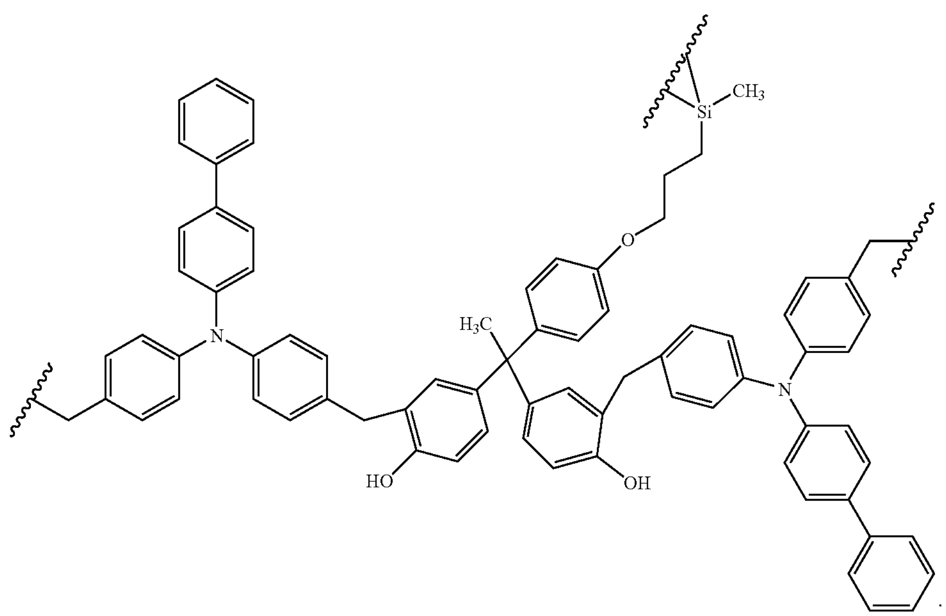

14. The electrophotographic imaging member of claim 1, wherein said outermost protective layer further comprises a polymeric binder resin selected from the group consisting of polyvinyl acetal resins, a polyamide resin, a cellulose resin, a phenol resin, and melamine-formaldehyde resin.

15. The electrophotographic imaging member of claim 14, wherein said polymeric binder is a polyvinylbutylral having a weight average molecular weight of from about 1000 to about 100,000.

* * * * *